(12) United States Patent
Anukhin et al.

(10) Patent No.: US 8,779,328 B2
(45) Date of Patent: *Jul. 15, 2014

(54) METHODS FOR LASER CUTTING TUBING TO MAKE MEDICAL DEVICES

(75) Inventors: Boris Anukhin, San Jose, CA (US); Larry Baughman, Campbell, CA (US); Pamela A. Kramer-Brown, San Jose, CA (US); Neil Burkhart, Fremont, CA (US); Li Chen, San Jose, CA (US); Duane M. DeMorre, Temecula, CA (US); Keif Fitzgerald, San Jose, CA (US); Gregory W. Johnson, Temecula, CA (US); Z. C. Lin, Palo Alto, CA (US); David Mackiewicz, Scotts Valley, CA (US); Karim S. Osman, Mountain View, CA (US); Randolf von Oepen, Los Altos, CA (US); William E. Webler, Jr., San Jose, CA (US); Travis R. Yribarren, Campbell, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1086 days.

This patent is subject to a terminal disclaimer.

(21) Appl. No.: 12/757,842

(22) Filed: Apr. 9, 2010

(65) Prior Publication Data
US 2010/0193485 A1 Aug. 5, 2010

Related U.S. Application Data

(63) Continuation-in-part of application No. 12/347,604, filed on Dec. 31, 2008, now Pat. No. 8,333,897, which is a continuation-in-part of application No. 11/756,305, filed on May 31, 2007, now Pat. No. 7,932,479.

(51) Int. Cl.
*B23K 26/38* (2014.01)
*B23K 26/40* (2014.01)
*A61F 2/06* (2013.01)
*A61F 2/07* (2013.01)

(52) U.S. Cl.
CPC .......... *B23K 26/4005* (2013.01); *B23K 26/402* (2013.01); *B23K 2201/04* (2013.01); *A61F 2/07* (2013.01)
USPC .................................................. 219/121.72

(58) Field of Classification Search
USPC ............... 219/121.67, 121.72, 121.84, 121.7, 219/121.71, 121.69, 121.66
See application file for complete search history.

(56) References Cited

U.S. PATENT DOCUMENTS

| 4,581,102 A | 4/1986 | Brock |
| 5,222,617 A | 6/1993 | Gregory et al. |

(Continued)

FOREIGN PATENT DOCUMENTS

| DE | 19831721 A1 | 1/2000 |
| DE | 19901530 A1 | 7/2000 |

(Continued)

OTHER PUBLICATIONS machine translation of Japan Patent document No. 5-92,207, Oct. 2013.*

(Continued)

*Primary Examiner* — Geoffrey S Evans
(74) *Attorney, Agent, or Firm* — Fulwider Patton LLP

(57) ABSTRACT

Methods for making devices include providing a tubular member to be formed into a device, placing a removable sacrificial block material in the lumen of the tubular member and laser cutting the tubular member. A tubular member made from nickel-titanium alloy can be tightly adhered to a sacrificial sleeve utilizing the phase changes associated with nickel-titanium. A mandrel which includes an enlarged diameter section causes the workpiece to expand slightly within its elastic deformation range to dislodge islands from the workpiece. Such a mandrel could be formed from a tubular member which has a central lumen that can be used to deliver a pressurized medium to "blast" islands from the workpiece.

20 Claims, 16 Drawing Sheets

(56) References Cited

U.S. PATENT DOCUMENTS

| | | | |
|---|---|---|---|
| 5,533,691 A * | 7/1996 | Doyle et al. | 242/597.4 |
| 5,560,883 A | 10/1996 | Lane et al. | |
| 5,759,192 A | 6/1998 | Saunders | |
| 5,780,807 A | 7/1998 | Saunders | |
| 5,994,667 A | 11/1999 | Merdan et al. | |
| 6,107,004 A | 8/2000 | Donadio, III | |
| 6,131,266 A | 10/2000 | Saunders | |
| 6,365,871 B1 | 4/2002 | Knowles et al. | |
| 6,369,355 B1 | 4/2002 | Saunders | |
| 6,521,865 B1 | 2/2003 | Jones et al. | |
| 6,537,459 B1 | 3/2003 | Dufresne et al. | |
| 6,679,980 B1 | 1/2004 | Andreacchi | |
| 6,696,667 B1 * | 2/2004 | Flanagan | 219/121.72 |
| 6,811,888 B2 | 11/2004 | Hamann et al. | |
| 6,865,810 B2 | 3/2005 | Stinson | |
| 6,888,098 B1 * | 5/2005 | Merdan et al. | 219/121.72 |
| 6,927,359 B2 | 8/2005 | Kleine et al. | |
| 8,278,593 B2 * | 10/2012 | Bialas et al. | 219/121.72 |
| 8,333,897 B2 * | 12/2012 | Bialas et al. | 219/121.72 |
| 2001/0019044 A1 * | 9/2001 | Bertez et al. | 219/121.72 |
| 2004/0015226 A1 | 1/2004 | Pelton | |
| 2005/0035101 A1 | 2/2005 | Jones et al. | |
| 2006/0054604 A1 * | 3/2006 | Saunders | 219/121.69 |
| 2006/0287715 A1 | 12/2006 | Atladottir et al. | |
| 2007/0191926 A1 * | 8/2007 | Nikanorov et al. | 623/1.15 |
| 2008/0296274 A1 | 12/2008 | Bialas | |

FOREIGN PATENT DOCUMENTS

| | | | |
|---|---|---|---|
| JP | 61-169188 | | 7/1986 |
| JP | 5-92207 A * | | 4/1993 |
| JP | 11-90661 A * | | 4/1999 |
| JP | 2001-212682 | | 8/2001 |
| WO | 0145578 A2 | | 6/2001 |

OTHER PUBLICATIONS machine translation of Japan Patent document Nio. 11-90,661, Oct. 2013.*

* cited by examiner

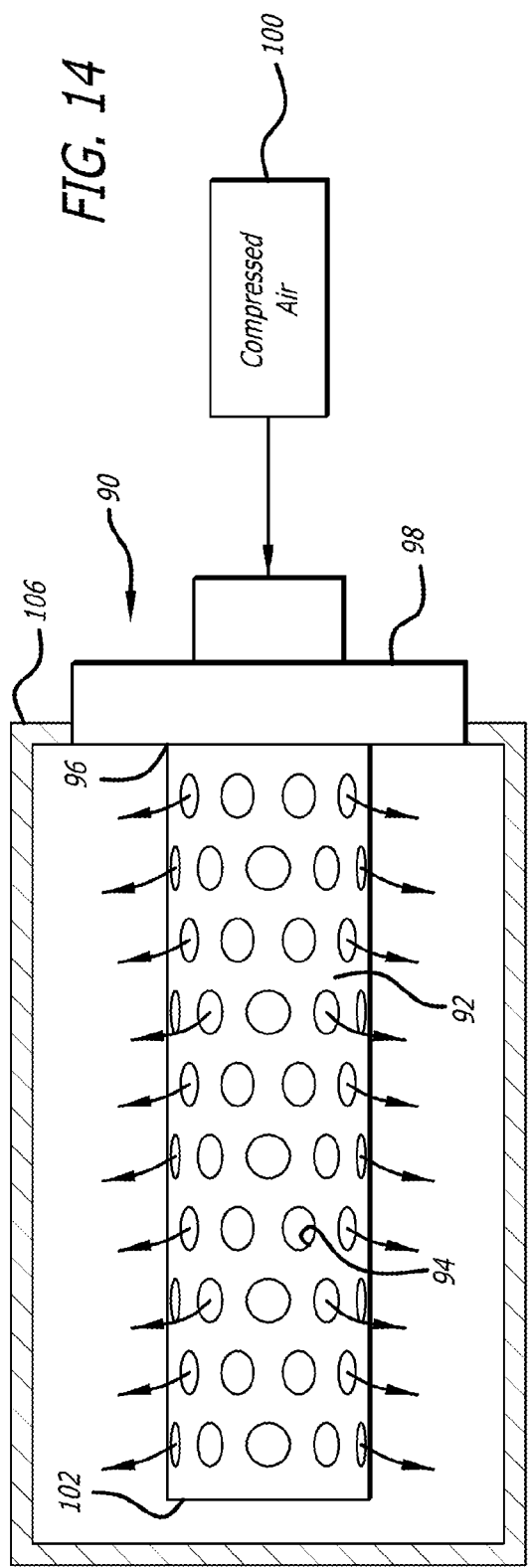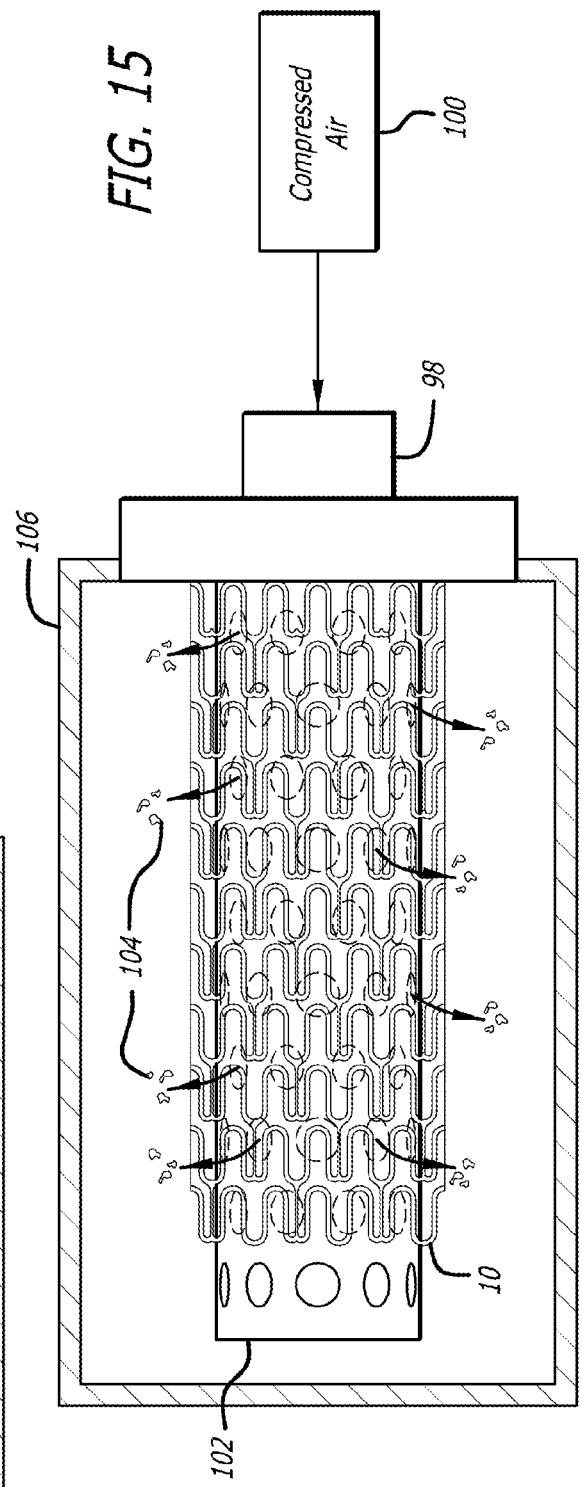

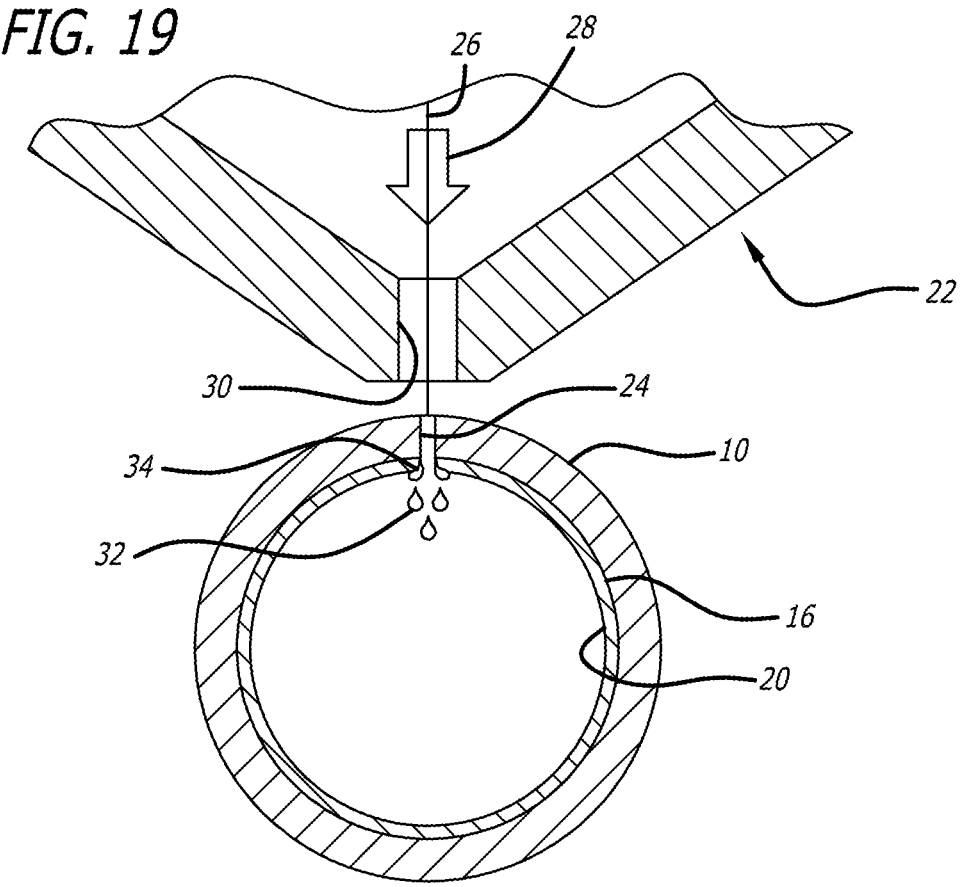
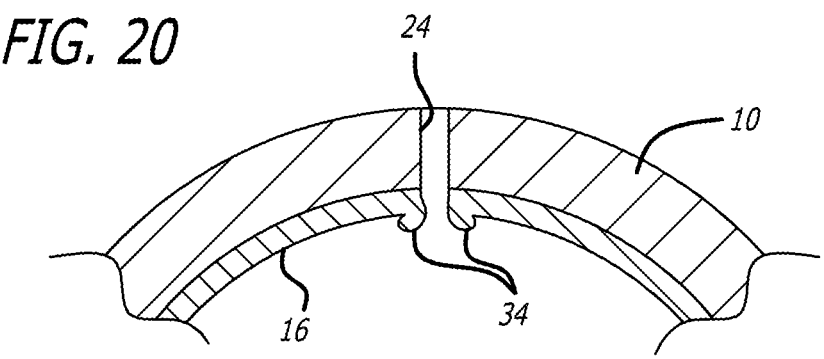

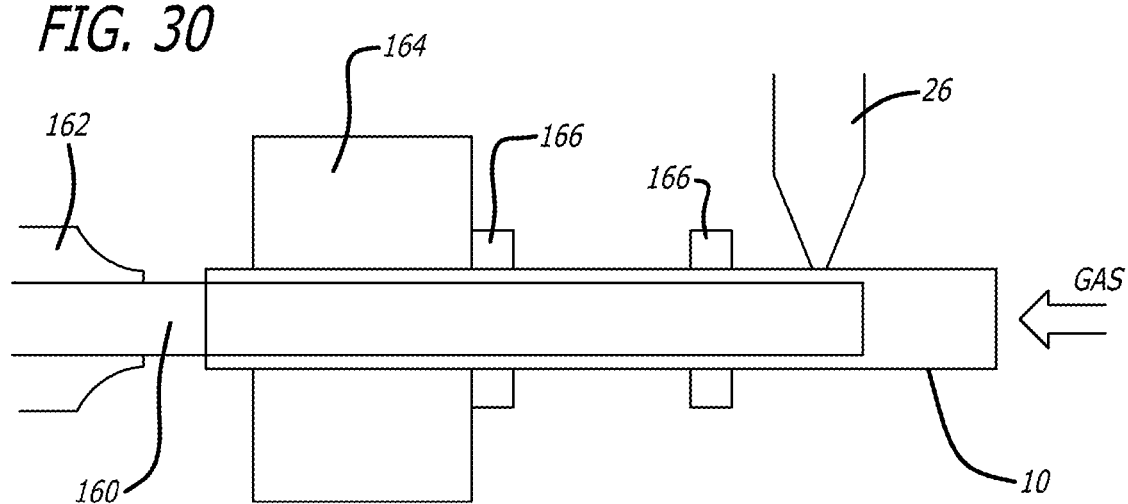
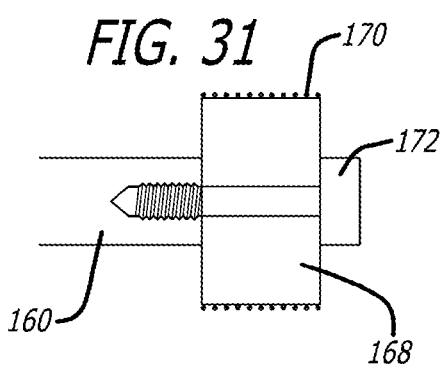
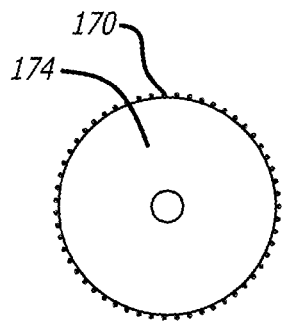
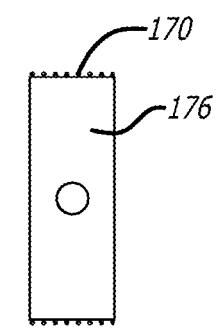
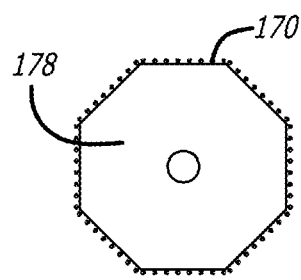
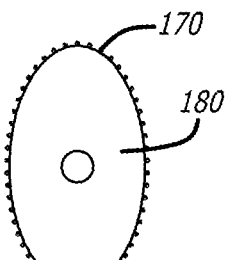
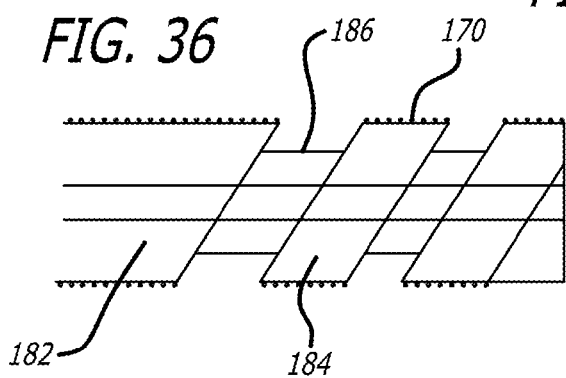

METHODS FOR LASER CUTTING TUBING TO MAKE MEDICAL DEVICES

CROSS-REFERENCE TO RELATED APPLICATIONS

This is a continuation-in-part application of U.S. Ser. No. 12/347,604, filed Dec. 31, 2008, which is a continuation-in-part application of U.S. Ser. No. 11/756,305, filed May 31, 2007, the contents of which are hereby incorporated by reference.

BACKGROUND OF THE INVENTION

The present invention relates generally to methods for laser cutting and processing a hollow workpiece, such as a length of tubing. The present invention is more particularly directed to methods for fabricating medical devices, such as, for example, expandable endoprostheses, commonly known as stents, using processes which help to prevent damage to the workpiece when cutting the workpiece with a laser apparatus and when later processing the cut workpiece.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the outcome of the procedure and reduce the possibility of restenosis.

Stents are generally cylindrically shaped devices which function to hold open, and sometimes expand, a segment of a blood vessel or other arterial lumen, such as a coronary artery. Stents are usually delivered in a compressed condition to the target site and then deployed at that location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self expanding stent formed from shape memory metals or super elastic nickel titanium alloys (Nitinol), which will automatically expand from a compressed state when the stent is advanced out of the distal end of the delivery catheter into the blood vessel.

Stents can be formed with strut patterns which when expanded have a large amount of open space, but when collapsed have little space between the often tortuously shaped struts forming the stent. One method of making a stent includes laser cutting a tubular member or tubing of suitable material to create the intricate strut patterns which define the structure of the stent. Laser cutting generally provides a precise method for forming these intricate strut patterns in the tubing used to form the stent. Such patterns require the tubing to be cut through one side of the wall of the tubing without cutting through the opposite side of the tubing.

In the past, laser apparatus utilizing pressured gas (oxygen) have been used to cut the tubing. Generally, a laser beam locally heats the tubing material while pressurized gas is blown through a small coaxial orifice directly onto the heated region in order to create a slot or "kerf" through the wall of the tubing. This pressurized gas, sometimes referred to as "shielding gas," forces the melted portion of the tubing into the inner lumen of the tubing where it will resolidify.

Laser cutting of a length of tubing generally begins by focusing a laser beam on a targeted spot on the tubing. The spot is melted and is preferably vaporized, or at least partially vaporized, by the laser beam. Once the laser beam burns through the side wall of the tubing, the beam will usually continue to strike the opposite side wall of the tubing, and may begin to vaporize, or partially vaporize, the opposite side wall of the tubing. This undesirable burning or partial vaporization of the opposite sidewall is called "burn through" and can result in the weakening of opposite sidewall. In some cases, burn through may result in the workpiece being discarded. The melting and vaporization of the tubing also can form "recast" material, which is material from the tubing that has melted and resolidified on laser-cut surfaces. The recast material, also referred to as "dross" and "slag," may include metal oxides and impurities which are undesirable in the manufacturing process since the recast material must be thoroughly removed from the surface of the stent. Oxidation can make a stent more susceptible to failure (e.g., cracking or fracture) during manufacturing or, if not completely removed, in use. Additionally, recast material can be particularly difficult to remove without damaging the thin struts created by the laser cutting operation. Therefore, both burn through and formation of recast material presents a formidable problem to the stent manufacturer.

The problems of laser cutting self-expanding stents made from a material such as Nitinol are further enhanced when pressurized air or oxygen is used to create the cut pattern. Because Nitinol is composed of about 50% titanium, a notoriously reactive metal, the titanium readily reacts with the oxygen in the air when heated. As a result, the material expelled during the cutting procedure is predominately comprised of metal oxides, most of which are trapped inside the tubing and adhere to the metallic inner surface of the Nitinol tube. Side walls of the slot or kerf also become oxidized during the cutting process, making the as-cut stent less ductile and thereby more susceptible to cracking or complete fracture during radial expansion or during other subsequent manufacturing steps. As a result, a laser cut Nitinol work piece must be carefully processed by a number of different cycles of chemical treatment, radial expansion, and heat stabilization to achieve the final stent size.

Any remaining oxidized wall material and other adhered oxide debris must first be removed in order to attain an acceptably smooth surface later during electropolishing. This additional clean up procedure can be achieved through a combination of automated grit blasting, manual grit blasting and chemical removal of oxide prior to electropolishing. Some methods require the physical removal of the recast material using a reamer or similar equipment and can often damage the thin struts of the stent. While electropolishing procedures can remove some recast material, often the recast material may be so heavily clad on the surface of the stent that not all of the recast material can be removed by this process. Additionally, the electropolishing process will remove material from the struts so it is important that only a small amount of the strut surface is actually removed. For example, if the electropolishing procedure is too long in duration, due to accumulated recast material, portions forming the struts of the stent may have too much material removed, resulting in a damaged or generally weakened stent.

Certain methods have developed to deal with the problem caused by burn through and the formation of recast material on the workpiece. One such method uses a continuous metal wire run through the tubular workpiece to create a "protective barrier" which somewhat helps to prevent the laser beam from striking the opposite sidewall of the tubing. Another system utilizes a liquid flushed through the workpiece as it is being cut. The fluid is usually fed through one end of the tubing and exits through the opposite end of the tubing, along with the newly formed openings in the wall of the tubing created by the laser. The liquid flushes away some of the recast material being created by the vaporization of the tubing. However, the presence of this liquid does not always completely block the laser beam, which can allow the inside wall of the tubing to be heated and damaged. Additionally, the use of liquid requires additional equipment for handling the liquid including discharge equipment, catch basins, waste disposal, and other processing equipment.

It has been anticipated that Nitinol stents could be laser cut using an inert gas such as argon or helium to prevent sidewall oxidation which would help prevent cracking or fracturing during subsequent processing. The absence of oxygen in the cutting process also will help to prevent the recast material from being oxidized. However, laser cutting Nitinol tubing utilizing pressurized argon gas typically cannot directly produce a finished stent because the expelled melted material formed during the cutting process can become "welded" to the inner wall of the tubing. This welded metallic build up could possibly be removed by later processing including reaming, drilling, electric discharge machining and the like but with difficulty and risk to the integrity of the workpiece.

What have been needed and heretofore unavailable are improved methods for reducing the adverse results caused by burn through along with the elimination of oxidation during the laser cutting process. Also, it would be beneficial to utilize additional equipment and processes to ease in subsequent cleaning, polishing and processing of the cut workpiece. The present inventions disclosed herein satisfy these and other needs.

SUMMARY OF THE INVENTION

The present invention is directed to methods for laser cutting a tubular workpiece which helps to reduce the number of post-cutting processing steps by preventing oxidation and preventing recast from adhering to the workpiece material during the laser cutting process. The present invention prevents oxidation of the workpiece by utilizing a laser apparatus that utilizes an inert gas, such as argon or helium, rather than air or oxygen, to create the slots or kerfs which form the pattern cut into the workpiece. The absence of oxygen in the cutting process thus prevents the workpiece from being oxidized during laser cutting. The present invention also utilizes a disposable, sacrificial mask which helps to prevent damage to the workpiece by covering the surface of the workpiece as it is being laser cut. The present invention is particularly beneficial in manufacturing intricately shaped devices from a hollow workpiece, such as a stent.

In one aspect of the invention, the disposable mask can be placed over at least a portion of the inner surface of the tubular member or tubing which is being laser cut. In the laser cutting process, recast material formed during the cutting process is forced through the kerf via the pressurized inert gas and is collected on the surface of the disposable mask, rather than on the inner surface of the tubular member. Tubing made from Nitinol can be laser cut using an inert gas without the risk of the recast material being welded onto the inner surface of the tubular member. During the cutting operation, both the tubular member and the disposable mask are simultaneously cut to the same pattern. During cutting, the expelled molten Nitinol collects on the inner surface of the disposable mask instead of directly on the inner surface of the tubular member, and afterward the expelled material and sacrificial mask can be removed because neither is strongly affixed to the inner surface of the Nitinol workpiece. Because the inert gas prevents oxidation of the sidewalls of the tubular member, the present invention allows the cut workpiece to be further processed with little or no need to grit blast tough oxidized material from the stent wall prior to electropolishing.

After the tubular member and sacrificial mask have been laser cut, there will be a build up of recast material formed along the bottom edges of the kerfs and elsewhere along the workpiece. Expelled molten material from the tubular member will collect on the inner surface of the sacrificial mask rather than being directly welded on to the inner surface of the tubular member. However, the recast material must still be removed from the laser-cut tubular member prior to electropolishing.

The present invention utilizes a variety of mechanical techniques to remove the sacrificial mask from the tubular member, along with a variety of chemical removal techniques which can be coupled with the mechanical techniques to quickly and cleanly remove the dross and sacrificial mask from the inner wall of the formed tubular member.

In one particular aspect of the present invention, the purely mechanical techniques for removing the dross and sacrificial mask is to attack the dross only, utilizing equipment which will grind, hone or bead-blast the dross only. Dross also can be removed utilizing a tool such as a wire brush or reamer. Another way to clean the lased tubular member would be to mechanically attack the sacrificial mask only. Similar mechanical techniques could be used to remove the sacrificial mask. Lastly, these same techniques could be used to mechanically attack both the dross and sacrificial mask. These various techniques provide simple but useful manufacturing steps to separate the lased tubular member from the sacrificial mask and dross.

In other aspects of the present invention, mechanical techniques to separate the components include employing different material properties between the lased tubular member and the sacrificial mask. For example, the tubular member and sacrificial mask could be made from different materials having different coefficients of thermal expansion. Application of heat or cold to the tubular member and sacrificial mask could then be used to break the sacrificial mask away from the lased tubular member.

In another mechanical procedure, a lased tubular member made from a self-expanding material, such as Nitinol, could be crushed and rolled to allow the tubular member to spring back to shape. Since the sacrificial mask is not superelastic, the crushing and rolling of the tubular member should break any connection between the sacrificial mask and the tubular member. Alternatively, the lased tubular member could be expanded, rather than being rolled, thereby causing the sacrificial mask to break away from the tubular member.

Still other removal procedures which can be implemented in accordance with the present invention include mechanically peeling the sacrificial mask from the lased tubular member or mechanically gripping and pulling/pushing the sacrificial mask out of the tubular member. Removal procedures could alternatively call for the tubular member/sacrificial mask to be subjected to vibration, which would break the sacrificial mask from the tubular member.

In another aspect of the present invention, the procedure for removing the sacrificial mask and dross from the lased tubular member would utilize a combination of chemical removal techniques with mechanical removal techniques, such as the ones addressed above. For example, after cutting, the lased tubular member and sacrificial mask can be subjected to a chemical attack which would only attack the tubular member material therefore dissolving the dross. A chemical solution would be applied to both the tubular member and sacrificial mask. The application of the chemical solution is designed to primarily attack the tubular member, rather than the disposable mask material. As such, the chemicals are selected which preferably attack the material of the tubular member, leaving the sacrificial mask material generally unharmed. In one aspect of the invention, the chemical solution attacks the tubular member by etching it. It should be noted that the recast material (especially the thin connection between the sidewall and recast metal) has a very large surface area to volume ratio and therefore it is much more readily attacked by the chemical solution than the body of the tubular member itself. This process of applying a chemical solution which primarily attacks the material forming the tubular member eliminates or weakens much of the recast material formed in the kerfs and elsewhere, thereby allowing the tubular member and the sacrificial mask material to be more easily separated.

After the chemical solution has acted on the tubular member, the tubular member and the sacrificial mask material are mechanically separated. This mechanical separation causes any recast material that is still adhering to the tubular member to be broken off, leaving the inner surface of the tubular member virtually free of any recast material. The removal of the sacrificial material from the inner surface of the tubular member can be performed mechanically, for example, by devices which will break the recast material formed in the kerfs and elsewhere. The mechanical process of removing the sacrificial material from the tubular member can be performed, for example, by inserting a mandrel into the inner lumen of the disposable mask and twisting the sacrificial mask from the inner surface of the tubular member. Any of the mechanical techniques mentioned above could be implemented to remove the sacrificial mask and any remaining dross from the tubular member.

In another aspect of the present invention, the removal process would encompass the application of a chemical solution which attacks only the sacrificial mask, leaving the tubular member virtually unharmed. The chemical attack can either dissolve the sacrificial mask completely, or could just weaken the sacrificial mask. Any one of a number of mechanical procedures could then be implemented to remove any remaining portions of the sacrificial mask and dross.

The removal process could encompass the application of chemicals which attacks both the sacrificial mask and tubular member. In this aspect of the invention, a chemical solution could first be applied which attacks or dissolves only the dross, then a second chemical solution could be applied which attacks only the sacrificial mask. Alternatively, the chemical solution which only attacks the sacrificial mask could be applied first and later the chemical solution which attacks the dross could be applied. In yet another removal procedure, a chemical solution which simultaneously attacks both the tubular member and sacrificial mask could be applied. In one scenario, the chemical solution could completely dissolve the sacrificial mask and dross. Alternatively, if the solution only weakens the dross and sacrificial mask, any remaining dross and mask material could be mechanically removed using any of the mechanical techniques mentioned above.

In another aspect of the invention, the disposable mask can take the shape of a tubular sleeve that is placed snugly against the inside surface of the tubular member. The disposable mask preferably assumes the form of a thin wall tube whose outer diameter closely matches the inner diameter of the tubular member. Alternatively, the mask may be comprised of a flat foil that is rolled into a cylinder and then inserted into the tubular member. In other aspects, the disposable mask may be produced through the build-up of material such as by electroplating, plasma spray, physical vapor deposition, chemical vapor deposition and the like. However, the disposable mask material should not become metallurgically bonded or otherwise so strongly affixed to the tubular member that the two components cannot be easily separated from each other after laser cutting. Additionally, the disposable mask and the work piece should be made from dissimilar materials that do not easily weld or bond to one another.

In one particular aspect of the present invention, steel such as stainless steel, is used to form the disposable mask when the workpiece is being formed from binary nickel-titanium or a nickel-titanium alloy due to the inherent metallurgical incompatibility of these materials. The disposable mask also could be made from any suitable material capable of withstanding the temperatures of the expelled molten Nitinol material, for example, ceramics, metals, composites, or high temperature polymers.

In another particular aspect of the present invention, carbon steel can be used to form the disposable mask when the workpiece is being formed from binary nickel-titanium or a nickel-titanium alloy due to the inherent metallurgical incompatibility of these materials. In one aspect, the disposable mask can be made from a carbon steel strip which is rolled or coiled into a sleeve that fits within the lumen of the tubular member. The strip of carbon steel creates a coiled sleeve which can expand radially within the lumen of the tubular member to ensure that a tight fit is made between the surfaces of the coiled sleeve and tubular member.

In another aspect of the present invention, the coiled sleeve and tubular member could be selectively lased removing a portion of the tubular member and coiled sleeve. After the laser cutting step, an acid etchant solution could be applied to the tubular member and coiled sleeve to erode the coiled sleeve. Any portion of the coiled sleeve which remains after the laser cutting would be eroded by the acid etchant. In another aspect, the acid etchant could be heated prior to application of the acid etchant to the tubular member and coiled sleeve. The acid etchant can be a mixture of hydrofluoric acid and nitric acid. In one aspect, the application of the acid etchant can be performed by placing the tubular member and coiled sleeve into a bath containing the acid etchant. The tubular member can be further processed by rinsing it with water and placing it in an ultrasonic bath containing alcohol.

In another aspect of the present invention, the process of making the device includes placing a sleeve made from a removable sacrificial material within the lumen of the tubular sleeve and co-drawing the tubular member and sleeve together. In this aspect of the invention, the co-drawing causes the surfaces of the sleeve and tubular member to come close together such that small spaces or gaps between the surfaces are eliminated or greatly reduced. The co-drawing of the tubular member and sleeve should be controlled to prevent the surfaces from molecularly bonding to each other. The tubular member and sleeve could then be laser cut with any remaining portion of sleeve being removed from the tubular member. In one aspect, the removal of any remaining portion of the sleeve can be done mechanically. In another aspect, the removal can be done chemically. In one particular aspect, any remaining portion of the sleeve can be chemically removed from the tubular member by applying a chemical solution to the tubular member and sacrificial material for a time duration in which the chemical solution primarily attacks the sacrificial material.

The pressurized inert gas used with the laser apparatus could be argon or helium as these two inert gases are economical and commercially available. However, it should be understood that the laser cutting of the tubular metallic work piece could utilize any inert or nonreactive, oxygen-free gas to prevent oxidation during the cutting process.

The use of the present method in forming a medical device, such as a stent, helps to minimize the need for grit blasting or otherwise chemically removing the oxidized cast material prior to electropolishing since air or oxygen is no longer used in the laser cutting process. The use of the inert gas eliminates the possibility that the sidewalls of the tubular member and recast material will become oxidized during laser cutting. As a result, the elimination of sidewall oxidation helps to prevent cracking or fracturing of the stent during use and eliminates some of the subsequent processing which would be otherwise be needed to remove the oxidized material from the tubular member. As a result, the formed workpiece can be sent for electropolishing without the need for additional processing which could break or irreparably damage the fragile struts which form the stent.

In yet another aspect of the present invention, the process of making the device includes applying ultrasonic energy to the tubular member as it is being laser cut into the desired shape of the workpiece. The application of ultrasonic energy to the tubular member helps top prevent slag from solidifying on the inner surface of the tubular member. The application of ultrasonic energy to the tubular member could be performed when the tubular member is being cut utilizing conventional laser cutting techniques already known in the art or could be used in conjunction with the novel sacrificial masks and processes disclosed herein.

In one particular aspect of the present invention, ultrasonic energy could be applied using an ultrasonic source, such as an ultrasonic transducer which includes a bushing that contacts the outer surface of the tubular member as it is being cut. The use of ultrasonic energy can be used in any laser cutting operation in which slag is formed and becomes problematic to the manufacturer since the slag will become deposited on a surface of the tubular member and will be required to be removed during subsequent processing.

In yet another aspect of the present invention, cleaning and polishing of the cut workpiece can be accomplished without application of excessive forces which could otherwise damage the often intricately cut workpiece. In this aspect, the cut tubular workpiece could be subjected to compressed air which will cause any slag affixed to the surface to be quickly removed. In one particular aspect, a mounting fixture having a number of outlet openings could be utilized to supply compressed air in the form of individual jets to the surface of the tubular workpiece. A compressed air supply would be connected to the mounting tube to supply the compressed air to the mounting fixture. The tubular workpiece would be slidable over the mounting fixture to allow the surface to be subjected to multiple jets of compressed air which will break most bonds between the slag and the surface of the workpiece. This process may eliminate the need to apply excessive force to the workpiece to break the slag from the surface. As a result, a greater yield of finished workpieces can be accomplished in less time than is normally needed to remove the slag using manual techniques.

In another aspect of the present invention, the disposable mask can be replaced with a solid sacrificial material in the form of a sacrificial block formed within the lumen of the tubular member. This sacrificial block is intended to fill substantially the entire lumen of the tubular member in order to protect the inner surface of the tubular member from the accumulation of recast slag. This sacrificial material can be made from a foam or foam-like material or a resin or resin-like material. Generally, these types of materials are initially in a liquid or semi-solid state and will solidify after a certain period of time or upon application of an agent or other source which transforms the liquid or semi-solid material into a solid structure. In this fashion, the inner lumen can be initially filled with this liquid or semi-solid material which will be allowed to harden to a more solid configuration. This solid sacrificial block allows the laser to more accurately cut the tubular member into the desired configuration since the solid block helps to counter the stresses acting on the tubular member as material is being removed during the laser process.

In another aspect of the present invention, the invention is directed to the formation of recast material or slag which is more brittle than slag which is normally generated during conventional laser processing. Since more brittle slag is much easier to remove in post polishing and removal steps, the overall manufacturing process can become more efficient and economical. This process can be implemented for any laser cutting method in which removal of slag is required. It is particularly applicable to laser cutting of Nickel-titanium alloys that include more challenging post-processing cleaning steps to be performed on the cut workpiece. In one embodiment, the assist gas used in conjunction with the laser can be modified as to its purity. By decreasing the purity of the assist gas below a certain threshold level, impurities in the assist gas will react with the molten material to form intermetallics that preferably embrittle the resulting slag material.

In another aspect of forming brittle slag, powder(s) can be mixed with the assist gas to form an aerosol which will create intermetallics when combined with the material make up of the tubular member. In this particular aspect, the melted portion of the tubular member becomes "doped" with a material (the added powder) which helps to create brittle slag.

In yet another aspect, a secondary gas may be directed to the flow of assist gas. This secondary gas may include powder(s) which can form intermetallics which attains more brittle slag. In yet another aspect, the consistency of the slag may be modified through the use of a sacrificial inner layer which will dope the slag as it recasts.

In another invention, an alternative method for post-processing the laser cut workpiece utilizes a fixture in which the workpiece is further processed. The fixture is made to have a slip fit between the outer diameter of the workpiece and the inner diameter of the fixture. The outer surface of the workpiece is initially glued or bonded to the inner surface of the fixture. This prevents the workpiece from twisting during the drilling/reaming process in which the sacrificial material is removed from the inner surface of the tubular member.

Another method of the present invention virtually eliminates any gap between the tubular member and the sacrificial sleeve. This aspect of the invention utilizes the self-expanding properties of the nickel-titanium alloy to creates a virtually gap free assembly. An oversized sacrificial sleeve is initially placed over a mandrel. The tubular member, which is made from nickel-titanium alloy, or similar self-expanding material, can then be transformed from its austinitic phase to its martensitic phase by cooling the tubular member using techniques well known in the art. The tubular member would be cooled down to a temperature below its AF temperature. Once in its martensitic state, the tubular member will be much softer and will allow the slightly oversized sacrificial sleeve to be placed within its inner lumen. The mandrel can then be removed once the sacrificial sleeve is properly in place. The tubular member can then be brought back to its austinitic phase by heating the tubular member to a high temperature, for example, room temperature. During transformation from the cooler martensitic state to the austenitic state, the tubular member will begin to shrink back to its initial diameter, which will create a very tight fit over the sacrificial sleeve. As a result, the tubular member will be tightly encased over the oversized sacrificial sleeve resulting in virtually no gap between these two components. The tubular member and sacrificial sleeve can now be lased to the desired pattern.

Another method and system for reducing the amount of slag distributed on a tubing inner diameter during laser cutting includes the use of pressurized gas being forced into the inner lumen of the tubular member. As the laser beam cuts through the tubing wall, the pressurization will force the melted material toward the outer surface of the tubing against the directional force of the laser and laser assist gas. Therefore, the inner diameter of the tubing will remain relatively clean as the slag is redistributed away from it.

Another system and method for reducing the formation of slag on the inner surface of the tubular member utilizes a rotating honing mandrel attached to a variable speed motor. This honing mandrel is designed to rotate within the inner lumen of the tubular member as it is being laser cut. Even though the honing mandrel is being struck by the laser beam, it does not burn or weld since it is designed to rotate during the laser cutting operation. The honing mandrel may include a surface in which a groove or channel is formed therein to act as a collection area for the recast material. In one particular embodiment, the channel or groove can be spiral in shape and extend along the length of the mandrel to create a collection area which allows the recast material to "flow" along this channel to the end on the mandrel where the material will fall out of the inner lumen of the tubular member. Thus, build up of recast material within the inner lumen can be reduced. The rotating mandrel may also include a surface portion which contacts, or is very close to making contact, with the inner surface of the tubular member. In this regard, this portion of the mandrel will "hone" or "scrape" the inner surface of the tubular member as the tubular member is being cut, thus removing molten material as it is being created during laser cutting. The outer surface of the mandrel may include a material which helps to scrape the molten material from the inner surface of the lumen. Such materials include, but are not limited to, abrasive coatings such as diamond, cubic boric nitride, plastics, glass and ceramics.

In another aspect of the present invention, cleaning and polishing of the cut workpiece can be accomplished by utilizing a mandrel which is capable of aiding in the removal or built-up slag or islands without application of excessive forces which could otherwise damage the often intricately cut workpiece. In this aspect, the cut workpiece could be placed on a mandrel which includes an enlarged diameter section. The cut workpiece could be slid over the enlarged diameter section which causes the workpiece to expand slightly within its elastic deformation range. Due to the minimal strains within the workpiece, it is expected that the workpiece will recover substantially to its original diameter. During expansion over the enlarged diameter section of the mandrel, the workpiece will undergo a physical separation from the slag or islands which may still be present on the cut workpiece. As the enlarged diameter section of the mandrel places a radial load on the workpiece, the islands will tend to dislodge from the workpiece and will be ejected from the pattern of the workpiece. Thus, as the workpiece reverts back to its normal diameter, there will be no, or significantly fewer islands remaining on the workpiece.

The mandrel can be made with a number of enlarged diameter sections which causes the workpiece to expand and contract as it moves along the mandrel. The enlarged diameter section can be made in various sizes (diameters and longitudinal lengths) and shapes (example, spherical, conical, irregular, etc). The mandrel could also be coupled to a source, such as, for example, an ultrasonic, rotating, or oscillating source, which helps to break up the islands formed on the workpiece. Alternatively, the surface of the mandrel could be coated with an abrasive material which hones or grinds the inner surface of the workpiece.

The mandrel with enlarged diameter section(s) could be formed from a tubular member which has a central lumen that can be used to deliver pressurized gases or fluids to direct the gas or liquid through openings formed on the mandrel to help "blast" islands from the workpiece. Such a mandrel also could be coupled to a source which provides, for example, ultrasonic, rotating, lubrication, to help to break up the islands formed on the workpiece. Alternatively, the surface of this mandrel could be coated with an abrasive material which hones or grinds the inner surface of the workpiece. As a result, a greater yield of finished workpieces can be accomplished in less time than is normally needed to remove the slag or islands using other manual techniques.

These and other advantages of the present invention become more apparent from the following detailed description of the invention, when taken in conjunction with the accompanying exemplary drawings.

BRIEF DESCRIPTION OF THE DRAWINGS

FIG. 14 is a top view showing a compressed air mounting fixture which discharges multiple jets of air to clean a tubular workpiece;

FIG. 15 is a top view showing a laser-cut tubular workpiece disposed on the compressed air mounting fixture of FIG. 14;

FIG. 19 is a schematic depiction of another embodiment of the present invention which utilizes a disposable sacrificial mask that mixes with the recast slag to form intermetallics to cause the material to become more brittle for easy removal from the workpiece;

FIG. 20 is a side elevational view showing the disposable mask of FIG. 19 and brittle recast material which is formed on the inner surface of the disposable mask;

FIG. 30 is a schematic representation of a system for making a device, such as a stent, from a tubular member using an argon gas laser and rotating honing mandrel which removes slag build up in the lumen of the tubular member during laser cutting;

FIG. 31 is a side view showing a honing component attached to the rotating mandrel;

FIG. 32 is an end view of the shape of one possible rotating mandrel made in accordance with the present invention;

FIG. 33 is an end view of the shape of one possible rotating mandrel made in accordance with the present invention;

FIG. 34 is an end view of the shape of one possible rotating mandrel made in accordance with the present invention;

FIG. 35 is an end view of the shape of one possible rotating mandrel made in accordance with the present invention;

FIG. 36 is a perspective view of an embodiment of a spiral mandrel made in accordance with the present invention;

DETAILED DESCRIPTION OF THE PREFERRED EMBODIMENTS

Figure 1:
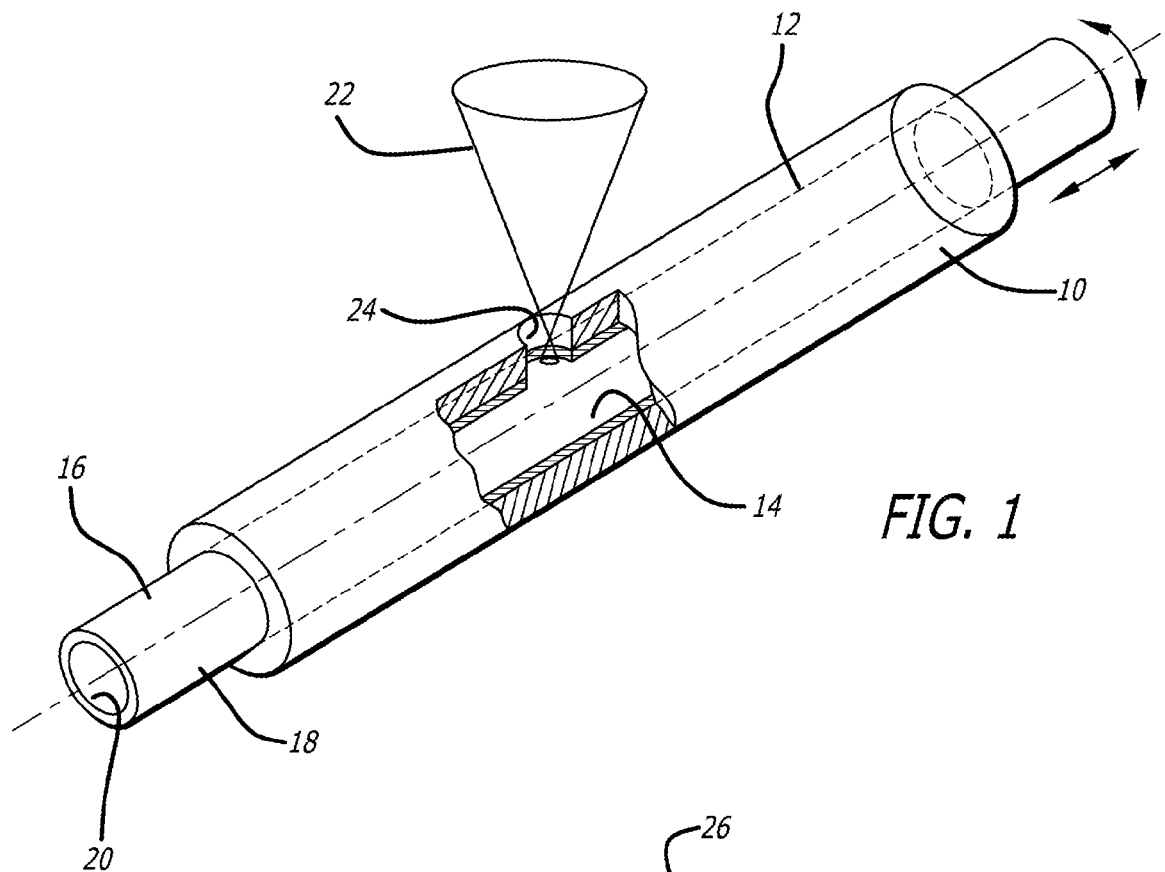
FIG. 1 is a perspective view showing a schematic of a method of making a device, such as a stent, from a tubular member using a laser device which uses an inert gas to assist in the cutting process.

Referring now to the drawing in which reference numerals represent like or corresponding elements across the drawings, and particularly FIGS. 1 and 3-5, a method of making a device from a hollow tubular member 10 is generally disclosed. The present invention relates generally to methods for laser cutting a length of hollow tubing, or as is it referred to herein a "tubular member," to form a device, typically a medical device, such as a stent. While most workpieces formed in accordance with the present invention are in the form of a tubular member having a circular cross section, the tubular member could have a non-circular cross section as well. For example, the tubular member could have a rectangular, oval, square, and the like cross section, if desired. Moreover, the invention is not limited to forming stents and has a wide application with respect to other laser cut medical devices and non-medical products, particularly products which require a high precision pattern that is cut utilizing a laser cutting process.

Referring specifically to FIG. 1, in one particular form of the present invention, the method includes providing a tubular member 10 which will be formed into the finished device. The tubular member 10 has an outer surface 12 along with an inner surface 14. The tubular member 10 is made from a particular material suitable for the finished device and is to be laser cut, as will be described herein, to generally form the desired pattern and shape of the finished workpiece. The present invention is particularly useful in cutting a tubular member made from a nickel-titanium alloy (Nitinol) or a ternary nickel-titanium alloy such as nickel-titanium-platinum. When a stent is being fabricated, the tubular member will be laser cut to remove portions of the tubular member to create the desired strut patterns of the stent. It should be appreciated that additional processing of the workpiece may be needed after initial laser cutting to achieve the final finished product.

As can be seen in FIG. 1, the tubular member 10 is shown in contact with a disposable mask made from a sacrificial material that will be simultaneously laser cut with the tubular member 10, but will be later removed in subsequent processing. This disposable mask, shown in this particular embodiment of the invention as a masking sleeve 16, is placed within the tubular member 10 to cover or mask at least a portion of the inner surface 14 of the tubular member 10. This masking sleeve 16 includes an outer surface 18 and an inner surface 20. The masking sleeve 16 is placed snugly against the inside surface 14 of the tubular member and can be later removed from contact with the tubular member 10. The disposable mask can be formed as a thin wall tube whose outer diameter closely matches the inner diameter of the tubular member 10. Generally, the disposable mask can have the same length, or can be larger or smaller than the length of the tubular member, depending, of course, on the amount of laser cutting to be performed on the tubular member 10. As is depicted in FIG. 1, the length of the masking sleeve 16 is longer than the length of the tubular member 10.

Figure 3:
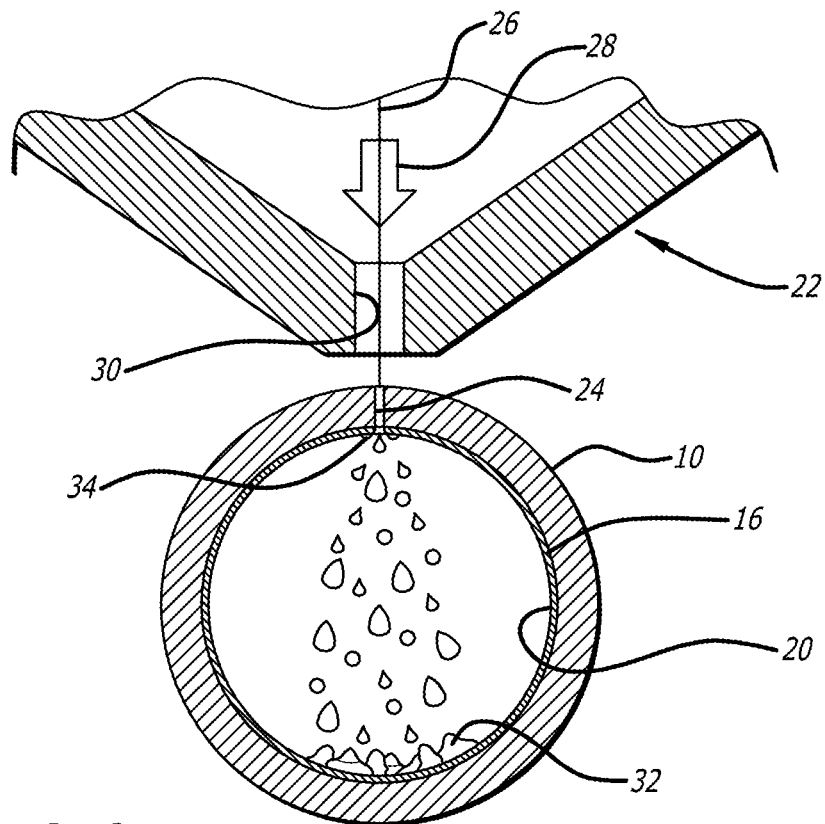
FIG. 3 is schematic side view showing the laser cutting of the tubular member mounted on a disposable sacrificial mask.

The method further includes the cutting of the tubular member 10 and masking sleeve 16 by laser cutting apparatus 22, shown schematically in the drawing figures. In one aspect of the present invention, the laser cutting apparatus 22 utilizes a pressurized inert gas, such as argon or helium, rather than air or oxygen, to create the slots or kerfs 24 extending through the wall of the tubular member 10 and masking sleeve 16. In the method of the present invention, both the tubular member 10 and masking sleeve 16 are cut simultaneously by the laser cutting apparatus 22. Generally, as is schematically depicted in FIG. 3, a laser beam 26 locally heats the tubular member 10 and masking sleeve 16 while the pressurized inert gas, depicted by arrow 28, is blown through a small coaxial orifice 30 directly onto the heated region in order to create the slots or kerfs 24.

Figure 2:
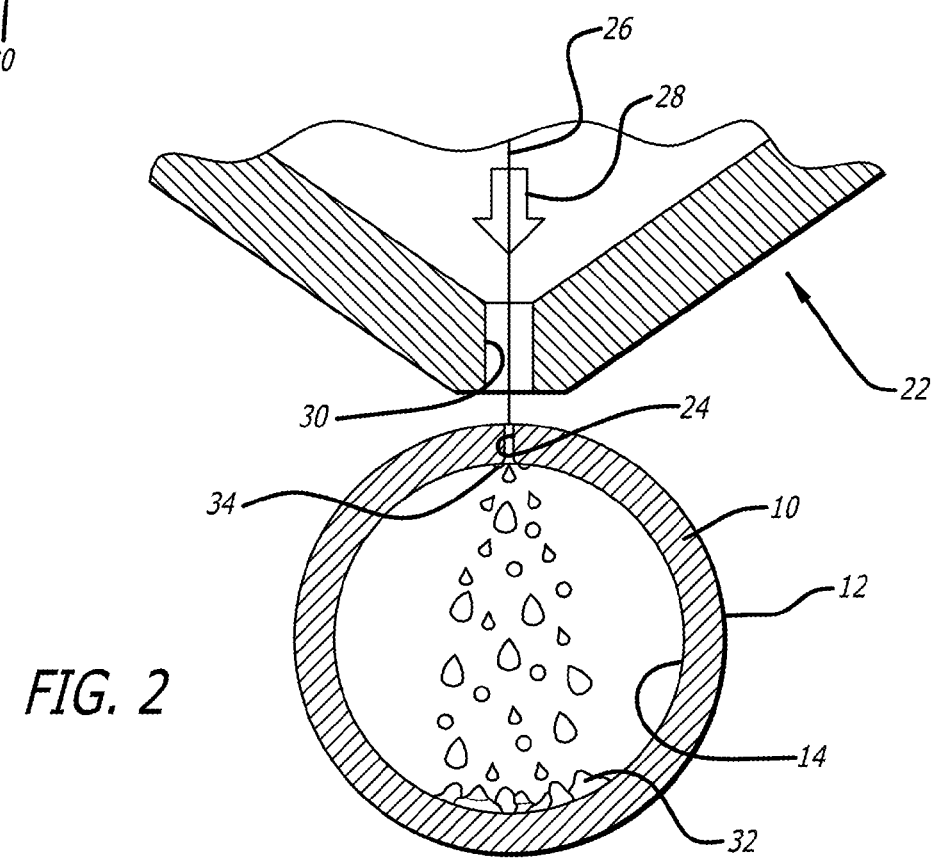
FIG. 2 is an end view showing the resulting formation of recast material on the inside surface of a tubular member when the laser cuts one side of the tubular member.

Laser cutting of the tubular member 10 and masking sleeve 16 generally begins by focusing a laser beam on a targeted spot on the tubing. The spot is melted by the laser beam while the pressurized inert gas forces the molten material through the walls of the tubular member and masking sleeve 16 to form the kerf 24. The tubular member 10 and sleeve 16 are moved by an automated mechanism of the laser cutting apparatus to create the desired pattern. Once the laser beam burns through the side wall of the tubular member 10 and masking sleeve 16, the laser beam could possibly continue to strike the opposite inside surface of the tubular member. However, the masking sleeve 16 covers the inner surface of the tubular member 10, thus preventing any damage to the tubular member. In the laser cutting process, recast material 32 which is forced through the kerf via the pressurized inert gas is collected as a disposable mass on the masking sleeve 16, rather than being "welded" to the inner surface 14 of the tubular member 10. In this aspect of the invention, the masking sleeve 16 forms a protective barrier for the inner surface 14 of the tubular member 10. FIG. 2 shows how the recast material would strike and damage the inner surface of the tubular member 10 if a disposable mask is not present. Also, since the inert gas prevents sidewall oxidation, the method of the present invention allows the cut work piece to be processed downstream without the need for substantial automated or manual grit blasting prior to electropolishing.

Figure 4:
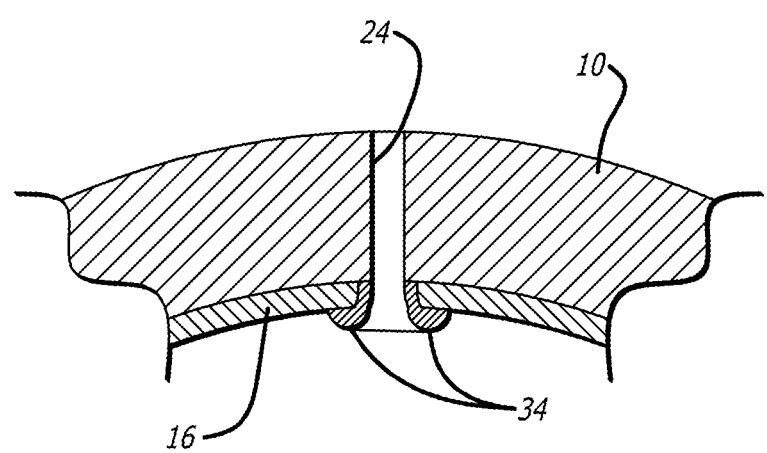
FIG. 4 is a side elevational view showing the resulting build up of recast material or "slag" along the bottom edge of the slot or kerf formed on the tubular member which must be removed prior to electropolishing.
Figure 5:
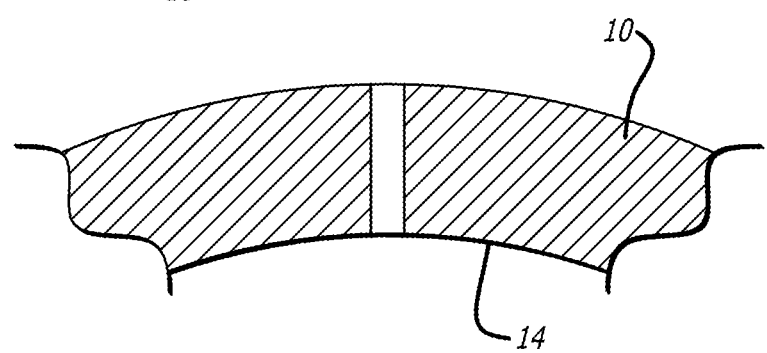
FIG. 5 is a side elevational view showing the disposable mask and recast material removed from the inner surface of the tubular member.

As is best depicted in FIG. 4, the laser cutting process not only results in the formation of recast material 32 disposed as bulk waste on the inner surface 20 of the masking sleeve 16, but also results in the formation of recast droplets 34 near the lower portion of the kerf 24. These recast droplets 34 cause portions of the tubular member 10 and masking sleeve 16 to somewhat bond together, forming an unwanted melded structure which must be removed from the tubular member 10 before additional processing proceeds. These recast droplets 34 are primarily solidified droplets of the material forming the tubular member 10.

The present invention utilizes a variety of mechanical techniques to remove the sacrificial mask and dross from the tubular member, along with a variety of chemical removal techniques which can be coupled with these mechanical techniques to quickly and cleanly remove the dross and sacrificial mask from the inner wall of the laser cut tubular member.

In one particular post-cutting procedure, the purely mechanical techniques for removing the dross and sacrificial mask is to attack the dross only, utilizing equipment which will grind, hone or bead-blast the dross only. For example, dross also can be removed utilizing a tool such as a wire brush or reamer. Another way to clean the lased tubular member would be to mechanically attack the sacrificial mask only. Similar mechanical removing techniques could be used to remove the sacrificial mask. Lastly, these same techniques could be used to mechanically attack both the dross and sacrificial mask. These various techniques provide simple but useful manufacturing steps to separate the lased tubular member from the sacrificial mask and dross.

The process of mechanically separating the disposable mask from the tubular member can use, for example, any type of device which will break the recast droplets and the contact between the surfaces of the tubular member and disposable mask. For example, the mechanical process of removing the sacrificial material from the tubular member can be performed by inserting a mandrel (not shown) into the lumen of the masking sleeve. The mandrel can be twisted causing the disposable mask to break contact with the inner surface 14 of the tubular member 10. The twisting action of the mandrel helps to peel the disposable masking material from the inner surface of the tubular member and break the bond created by the recast material and droplets. The surface of the mandrel could include prongs, flutes, knurling or other friction enhancing structure which increases frictional contact between the mandrel and disposable mask. It should be appreciated that other means for mechanically removing the disposable mask from the tubular member can be utilized in accordance with the present invention.

Another particular mechanical technique for removing the sacrificial mask and dross from the tubular member would require the separation of the components by employing different material properties between the lased tubular member and the sacrificial mask. For example, the tubular member and sacrificial mask could be made from different materials having different coefficients of thermal expansion. For example, heat or coldness could be applied to the cut work piece to cause the tubular member to either expand or contract, which should break the sacrificial mask away from the lased tubular member. Alternatively, the sacrificial mask could be made from a material which will expand or contract upon application of heat or coldness to cause the mask to break away from the tubular member.

In another mechanical procedure, a lased tubular member made from a self-expanding material, such as Nitinol, could be crushed and rolled to allow the tubular member to spring back to shape. The sacrificial mask could be made from a material which is comparatively not very elastic, so that the crushing and rolling of the tubular member should break any connection between the sacrificial mask and the tubular member. Alternatively, the lased tubular member could be expanded, rather than being rolled, which again should cause the sacrificial mask to break away from the tubular member.

Still other removal procedures which can be implemented in accordance with the present invention include mechanically peeling the sacrificial mask from the lased tubular member or mechanically gripping and pulling/pushing the sacrificial mask out of the tubular member. A reamer or mandrel could be used to grip the inside surface of the sacrificial mask to allow a technician to pull or push the mask from the tubular member. Other tools could be implemented as well to accomplish this type of mechanical removal. Additionally, removal procedures could alternatively call for the laser cut tubular member/sacrificial mask to subjected to vibration, which would break the sacrificial mask from the tubular member.

In another aspect of the present invention, the procedure for removing the sacrificial mask and dross from the lased tubular member would utilize a combination of chemical removal techniques with mechanical removal techniques, such as the ones addressed above, to achieve a clean workpiece which is ready for electropolishing. For example, after cutting, the lased tubular member and sacrificial mask can be subjected to a chemical attack which would only attack the tubular member itself, i.e. the dross. A chemical solution would be applied to both the tubular member and sacrificial mask. The application of the chemical solution is designed to primarily attack the tubular member, rather than the disposable mask material. As such, the chemicals are selected which preferably attack the material of the tubular member, leaving the sacrificial mask material generally unharmed. In one aspect of the invention, the chemical solution attacks the tubular member by etching it.

The process for removing the recast material and droplets from the tubular member requires a chemical solution to be applied to both the tubular member 10 and masking sleeve 16. The chemical solution can be directly applied to the tubular member 10 and masking sleeve 16 or the components could be dipped into a bath containing the chemical solution. The chemical solution is designed to primarily attack the tubular member 10, leaving the masking sleeve unharmed. It should be noted that the recast droplets 34 have a very large surface area to volume ratio and therefore they are much more readily attacked by the chemical solution than the larger body of the tubular member 10 itself. This process of applying a chemical solution which primarily attacks the tubular member 10 eliminates or weakens much of the recast droplets 34, thereby allowing the tubular member 10 and the masking sleeve 16 to be more easily separated.

After the chemical solution has acted on the tubular member, the tubular member and the sacrificial mask material can be further processed, if needed, using mechanical separation procedures. This mechanical separation causes any recast material that is still adhering to the tubular member to be broken off, leaving the inner surface of the tubular member virtually free of any recast material. After the chemical solution is applied to the tubular member 10 and masking sleeve 16 and the recast material is weakened, the tubular member and the masking sleeve 16 should be relatively easy to separate using mechanical techniques. Since the masking sleeve is virtually unharmed by the chemical solution, it remains stiff and capable of breaking the recast material formed at the kerfs when twisted away from the tubular member. Any recast material or droplets 34 that still adhere to the tubular member 10 will be broken off, leaving the inner surface 14 of the tubular member 10 virtually free of any recast material.

The removal of the sacrificial material from the inner surface of the tubular member can be performed mechanically, for example, by devices which will break the recast material formed in the kerfs and elsewhere. The mechanical process of removing the sacrificial material from the tubular member can be performed, for example, by inserting a mandrel into the inner lumen of the disposable mask and twisting the sacrificial mask from the inner surface of the tubular member. Any of the mechanical techniques mentioned above could be implemented to remove the sacrificial mask and any remaining dross from the tubular member, after the chemical application has been completed.

In another aspect of the present invention, the process of removing the mask and dross from the tubular member would encompass the application of a chemical solution which attacks only the sacrificial mask, leaving the tubular member virtually unharmed. The chemical attack can either dissolve the sacrificial mask completely, or could just weaken the sacrificial mask. Any one of a number of mechanical procedures could then be implemented to remove any remaining portions of the sacrificial mask and dross.

The removal process could encompass the application of chemicals which attacks both the sacrificial mask and tubular member. In this process, a chemical solution could first be applied which attacks or dissolves only the dross. Thereafter, a second chemical solution could be applied which attacks only the sacrificial mask. Alternatively, the chemical solution which only attacks the sacrificial mask could be applied first and later the chemical solution which attacks the dross could be applied. In yet another removal procedure, a chemical solution which simultaneously attacks both the tubular member and sacrificial mask could be applied. In one scenario, the chemical solution could completely dissolve the sacrificial mask and dross, eliminating the need for any further mechanical separation. Alternatively, if the chemical solution only weakens the dross and sacrificial mask, any remaining dross and mask material could be mechanically removed using any of the mechanical techniques mentioned above.

The use of the present method in forming a medical device, such as a stent, reduces the amount of grit blasting or chemical removal due to the lack of oxidized cast material since air or oxygen is no longer used in the laser cutting process. Again, the use of the inert gas eliminates the possibility that the sidewalls or the recast material will be oxidized during the laser cutting step. As a result, the elimination of sidewall oxidation helps to prevent cracking or fracturing of the stent during use and reduce or even eliminates some of the subsequent processing which would be otherwise utilized in order to remove the oxidized material from the tubular member. As a result, the formed stent can be sent for electropolishing without the need for additional processing, or with only a minimal amount of mechanical processing, which reduces the chance of breaking or irreparably damaging the often fragile struts forming the stent.

Although the sacrificial mask is disclosed herein as a disposable masking sleeve, it should be appreciated that other forms and configurations of a disposable sacrificial mask could be used in accordance with the present invention. For example, the mask may be comprised of a flat foil that is rolled into a cylinder and then inserted into the tubular member. Additionally, the disposable mask could be produced through the build-up of material on the inner surface of the tubular member by such methods as electroplating, plasma spraying, physical vapor deposition, chemical vapor deposition and the like. However, it is important that the disposable sacrificial mask material does not become metallurgically bonded or otherwise so strongly affixed to the tubular member that the two components cannot be easily separated from each other after laser cutting and the application of the mechanical and/or chemical processing of the cut workpiece. Thus, the disposable mask and the tubular member should preferably be made from dissimilar materials that do not easily weld or bond to one another. In one particular method of the present invention, steel or stainless steel can be used to form the disposable mask when a Nitinol tubular member is being fabricated because of their inherent metallurgical incompatibility. For example, the disposable mask could be formed from any material capable of withstanding the temperatures of the expelled molten material, such as ceramics, metals, composites, or high temperature polymers. Other suitable metals include steel, copper, magnesium, nickel, cobalt, molybdenum, tantalum, niobium, titanium, zirconium, tin, iron, or any other alloy based on these metals.

The pressurized inert gas used with the laser cutting apparatus may include argon or helium, which are preferred because they are economical and commercially available. However, it should be understood that the laser cutting apparatus could utilize any inert gas to prevent the work piece from oxidizing. Since argon and helium gases are more readily available commercially, these inert gases may serve to be more economical from a cost standpoint.

One particular method of chemically attacking the tubular member results in the material forming a tubular member to be etched away to weaken any recast material remaining on the workpiece. In this particular method of the present invention, a nickel-titanium or a ternary nickel-titanium alloy is the material used to form the tubular member and stainless steel is used to form the disposable mask. The tubular member and mask can be immersed in a solution of approximately 3% hydrofluoric acid (HF) and 50% nitric acid to chemically etch the recast material formed by the tubular member to help break the strength of the bond created by the recast material. The acid can rapidly etch away at the nickel-titanium alloy while the stainless steel disposable mask remains relatively undamaged. In this aspect of the invention, the acid will leave the stainless steel material relatively unharmed. The submersion of these two components in the hydrofluoric acid can be for a time duration from approximately 30-45 seconds, after which the components are removed. If needed, the mechanical process of removing the disposable mask from the tubular member can then be performed. In another variation, a steel sleeve could be used and the aforementioned HF-nitric solution could be used to simultaneously and completely dissolve both the steel sleeve and nitinol dross in only 10-20 seconds. This embodiment is particularly useful when the workpiece is particularly long or delicate therefore making the mechanical removal of the sleeve difficult. It should be appreciated that other chemical solutions could be utilized in accordance with the present invention. For example, the chemical solution can be acidic, alkaline, or any other chemically reactive agent which preferably attacks the tubular member rather than the disposable mask material or simultaneously attacks both. The strength of the chemical solution and the time duration that the chemical solution remains on the components will depend, of course, on the type of materials used for the tubular member and disposable mask and the type of chemical utilized.

Figure 8:
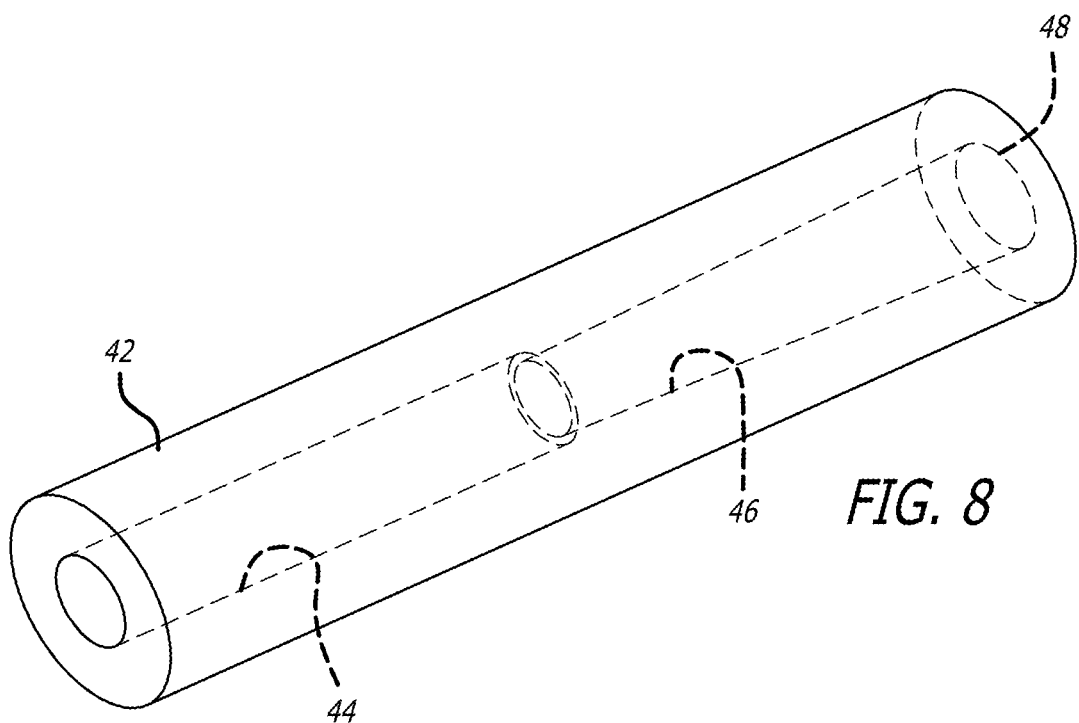
FIG. 8 is a perspective view of a tool which draws down the rolled carbon steel sleeve of FIGS. 6 and 7 in order to fit within a tubular member.
Figure 9:
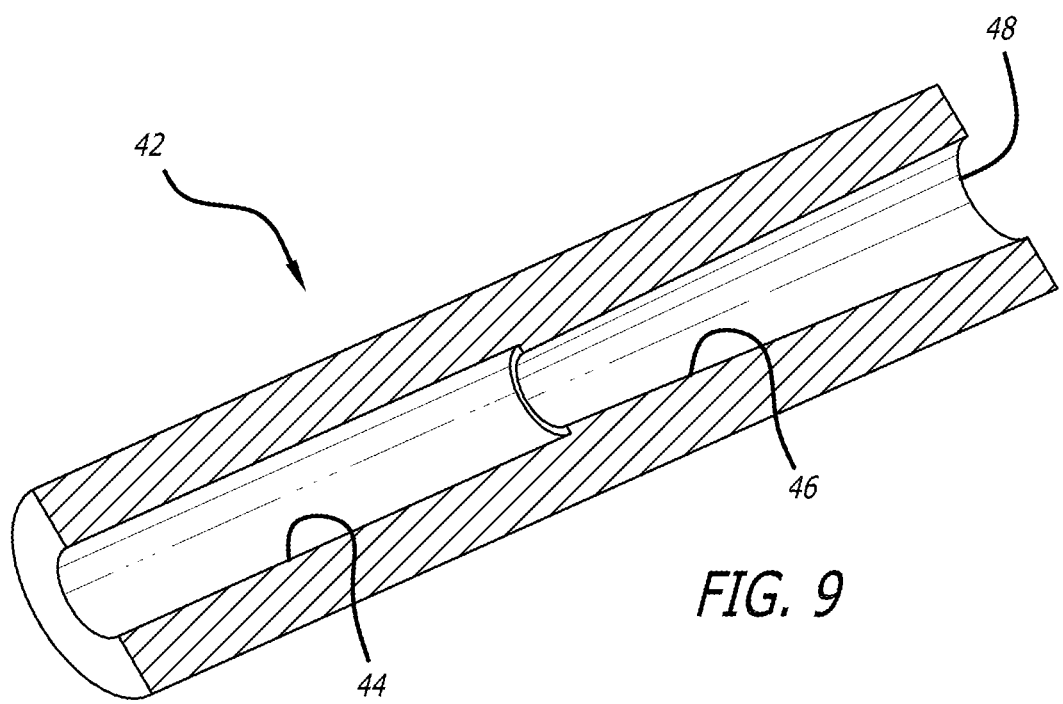
FIG. 9 is a cross-sectional view of the tool of FIG. 8.
Figure 10:
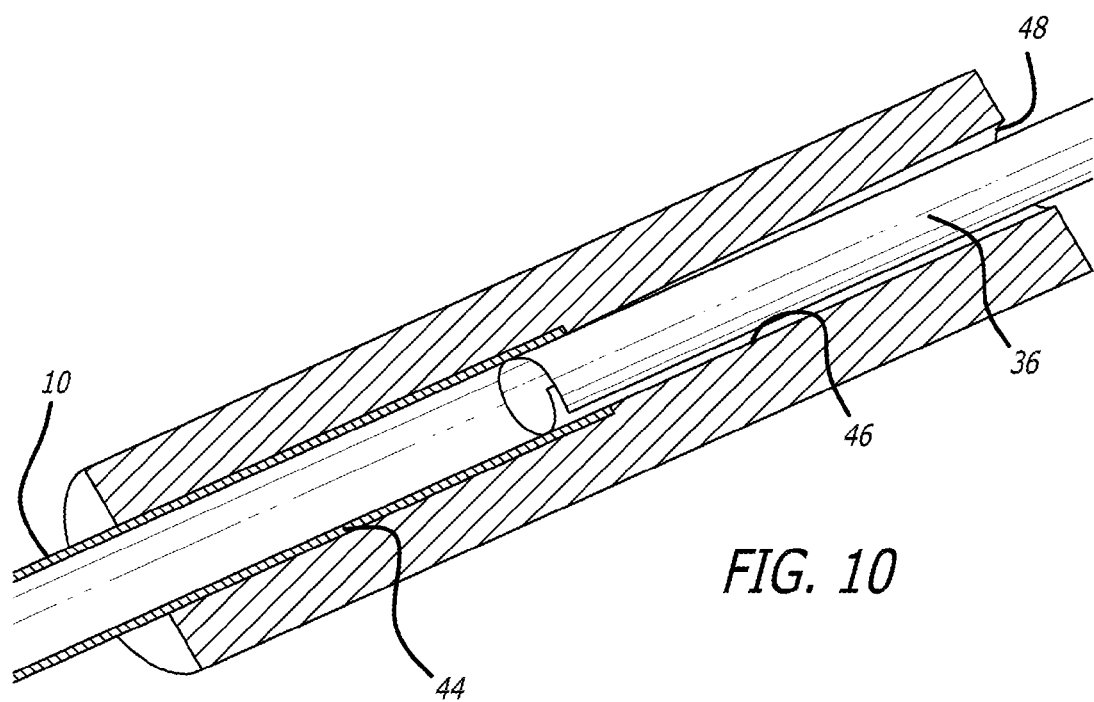
FIG. 10 is a cross-sectional elevational view showing the rolled sleeve of FIGS. 6 and 7 being drawn down by the tool of FIGS. 8 and 9 in order fit the rolled sleeve into a tubular member.

Referring now to FIGS. 6-10, the disposable mask can be made from a strip of material which is rolled or coiled into a sleeve 36. This coiled sleeve 36, in turn, fits within the lumen of the tubular member 10 (FIG. 10). The strip of carbon steel creates a coiled sleeve 36 having an outer surface 38 which contacts the inner surface 14 of the tubular member 10. The coiled sleeve 36 is biased somewhat so that it can expand radially within the lumen of the tubular member 10 to ensure that a tight fit is made between the surface 30 of the coiled sleeve 36 and the surface 14 of the tubular member 10. This coiled sleeve 36 can be used in any of the method disclosed herein.

Figure 6:
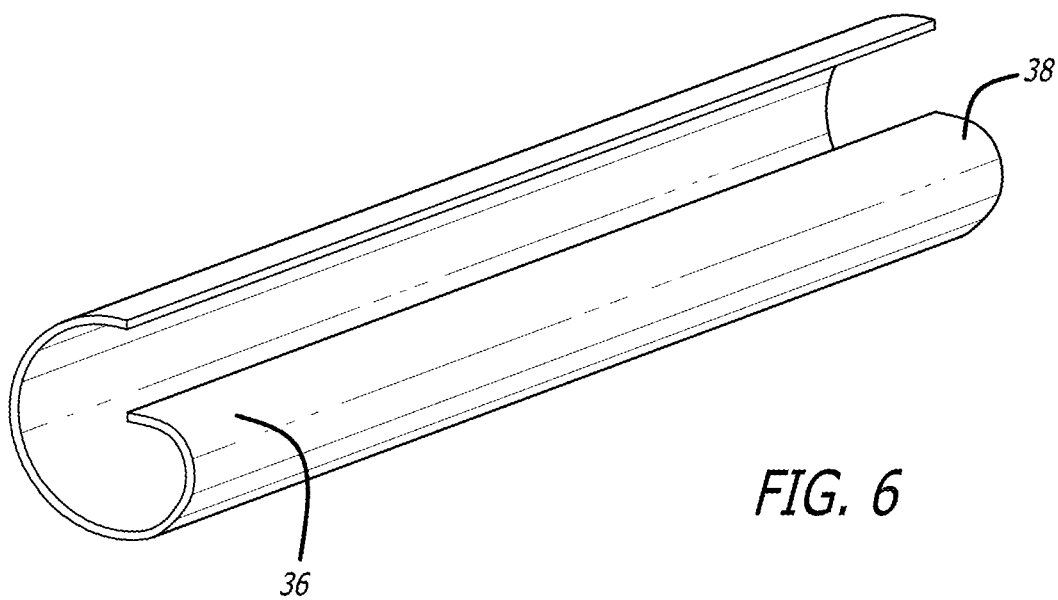
FIG. 6 is a perspective view of a carbon steel sleeve which is rolled to create a disposable sacrificial mask in accordance with the present invention.
Figure 7:
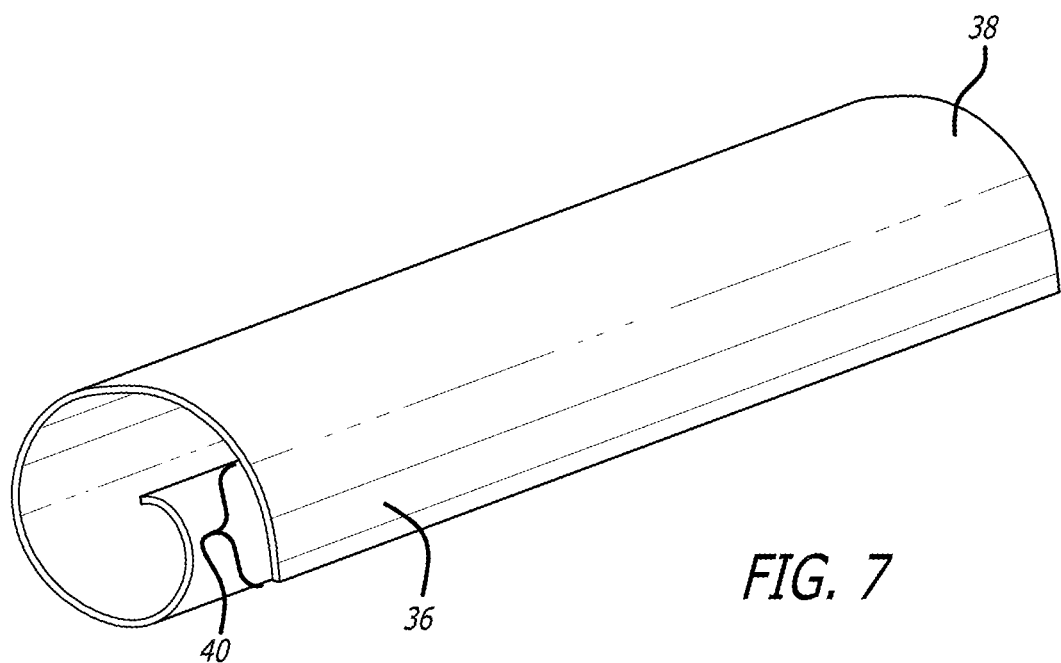
FIG. 7 is a perspective view of the rolled carbon steel sleeve of FIG. 6 which shows a portion of overlap of the sleeve.

As can be seen in FIG. 7, there is a slight overlap 40 of material forming the coiled sleeve 36. This overlap 40 allows the sleeve 36 to expand radially outward to contact the inner surface of variously sized tubular members. In this aspect, the coiled sleeve can be used in a number of tubular members having different diameters. In this fashion, the coiled sleeve will expand to the particular inner diameter of the tubular member in which it is placed. Thus, the use of a coiled sleeve eliminates the need to manufacture individually sized sleeves for use with particularly sized tubular member. Hence, one coiled sleeve can be placed in a number of different sized tubular members. While the particular embodiment of the coiled sleeve 36 of FIGS. 6 and 7 shows an overlap 40 ranging about 20° of the full 360° of the circle forming the diameter of the sleeve, it should be appreciated that more or less of an overlap 40 could be used on the coiled sleeve 36 as well. This overlap 40 represents the amount of material which overlaps when the coiled sleeve is in its maximum outside diameter. As will be discussed below, this maximum outside diameter can be reduced to a minimum outside diameter by applying a force to the coiled sleeve.

A tool 42, shown in FIGS. 8-10, can be used to place the coiled sleeve 38 within the lumen of the tubular member 10. This tool 42 is simply a structural member having two lumens extending therethrough. The first lumen 44, is used to hold the tubular member 10 as is shown in FIG. 10. The second lumen 46, is used to move the coiled spring into the lumen of the tubular member 10. In this regard, this second lumen may be tapered so that a larger diameter is located at the opening 48 through which the coiled sleeve is inserted. The second lumen tapers to a smaller diameter which causes the coiled sleeve to contract to a smaller diameter as it is further inserted into the second lumen 46. In turn, the smaller diameter of this second lumen 46 draws the coiled sleeve down to properly fit within the lumen of tubular member 10, as is shown in FIG. 10. A plunger (not shown) could be applied to the end of the coiled sleeve to help push the coiled sleeve 36 into the tubular member. Once the coiled sleeve is placed within the lumen of the tubular member 10, it will radially expand to create force that maintains tight contact between the surface 38 of the sleeve 36 and the inner surface 14 of the tubular member 10. It should be appreciated that other tools and methods could be utilized to place the coiled sleeve within the lumen of the tubular member.

In another particular aspect of the present invention, carbon steel can be used to form the coiled sleeve 36, although other material listed above could also be used to create the sleeve. In one particular method of making a device, the coiled sleeve could be placed within the lumen of the tubular member. The coiled sleeve 36 and tubular member 10 could be selectively lased removing a portion of the tubular member and coiled sleeve. After the laser cutting step, an acid etchant solution could be applied to the tubular member and coiled sleeve to erode the coiled sleeve. Any portion of the coiled sleeve which remains after the laser cutting would be eroded by the acid etchant. The acid etchant could be heated prior to application of the acid etchant to the tubular member and coiled sleeve. The acid etchant can be a mixture of hydrofluoric acid and nitric acid. In one aspect, the application of the acid etchant can be performed by placing the tubular member and coiled sleeve into a bath containing the acid etchant The tubular member can be further processed by rinsing it with water and placing it in an ultrasonic bath containing alcohol.

In one particular example, a strip of 0.003 inch thick carbon steel having a width of about 0.33 inches is rolled into a tubular shape, as shown in FIG. 7. The length of the piece is about 24-27 inches to match the length of the nitinol tubing used to create the device. In this case, the device to be created is a self-expanding stent. The width of the strip is sufficient to achieve a coiled sleeve having an outside diameter of about 0.1005 inches with about a 20° overlap when coiled in its maximum outside diameter. The coiled sleeve can be rolled or coiled in order to achieve a minimum outside diameter of about 0.095 inches. Thus, the range of expected inside diameters for the nitinol tubing would be from 0.095 to 0.1005 inches. It should be appreciated that the various sizes of the strips used to create the coiled sleeves will depend upon the various size of the tubular member which will eventually be formed into the desired device.

Figure 11:
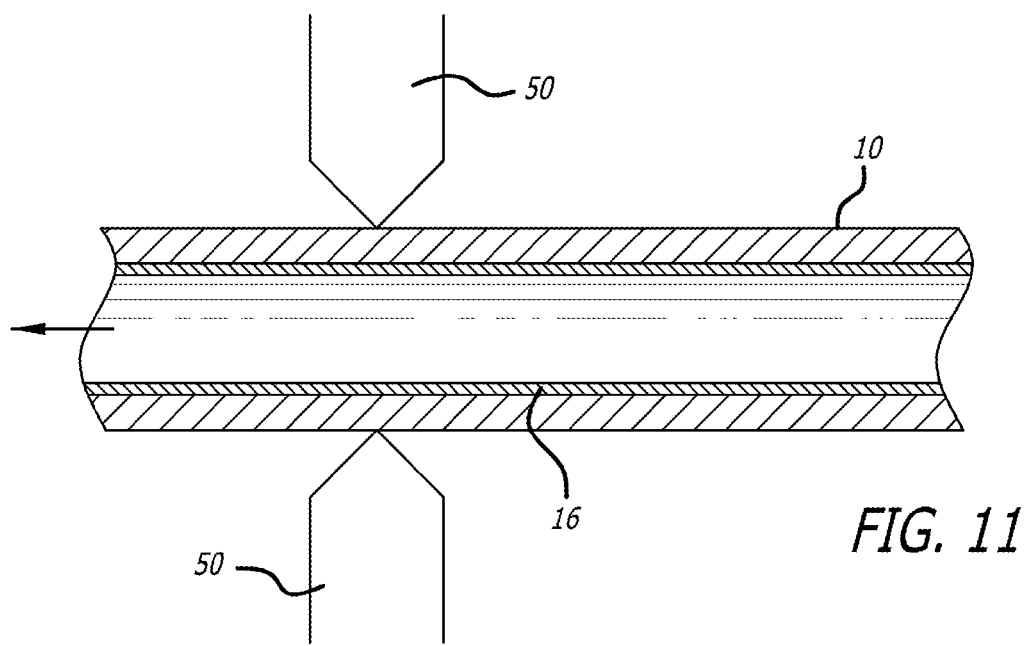
FIG. 11 is a cross-sectional view showing a disposable sacrificial mask and tubular member which undergo a co-drawing process prior to laser cutting.

In another aspect of the present invention, the process of making the device includes placing a sleeve made from a removable sacrificial material within the lumen of the tubular sleeve and co-drawing the tubular member and sleeve together. FIG. 11 schematically shows the sleeve 16 and tubular member being drawn together through a die 50. Still other ways of co-drawing the sleeve and tubular member can be achieved. In this aspect of the invention, the co-drawing causes the surfaces of the sleeve and tubular member to come close together such that small spaces or gaps between the surfaces are eliminated or greatly reduced. The co-drawing of the tubular member and sleeve should be controlled to prevent the surfaces from molecularly bonding to each other. The tubular member and sleeve could then be laser cut with any remaining portion of sleeve being removed from the tubular member. In one aspect, the removal of any remaining portion of the sleeve can be done mechanically. In another aspect, the removal can be done chemically. In one particular aspect, any remaining portion of the sleeve can be chemically removed from the tubular member by applying a chemical solution to the tubular member and sacrificial material for a time duration in which the chemical solution primarily attacks the sacrificial material. The sleeve can be made from any of the materials listed above.

Figure 12:
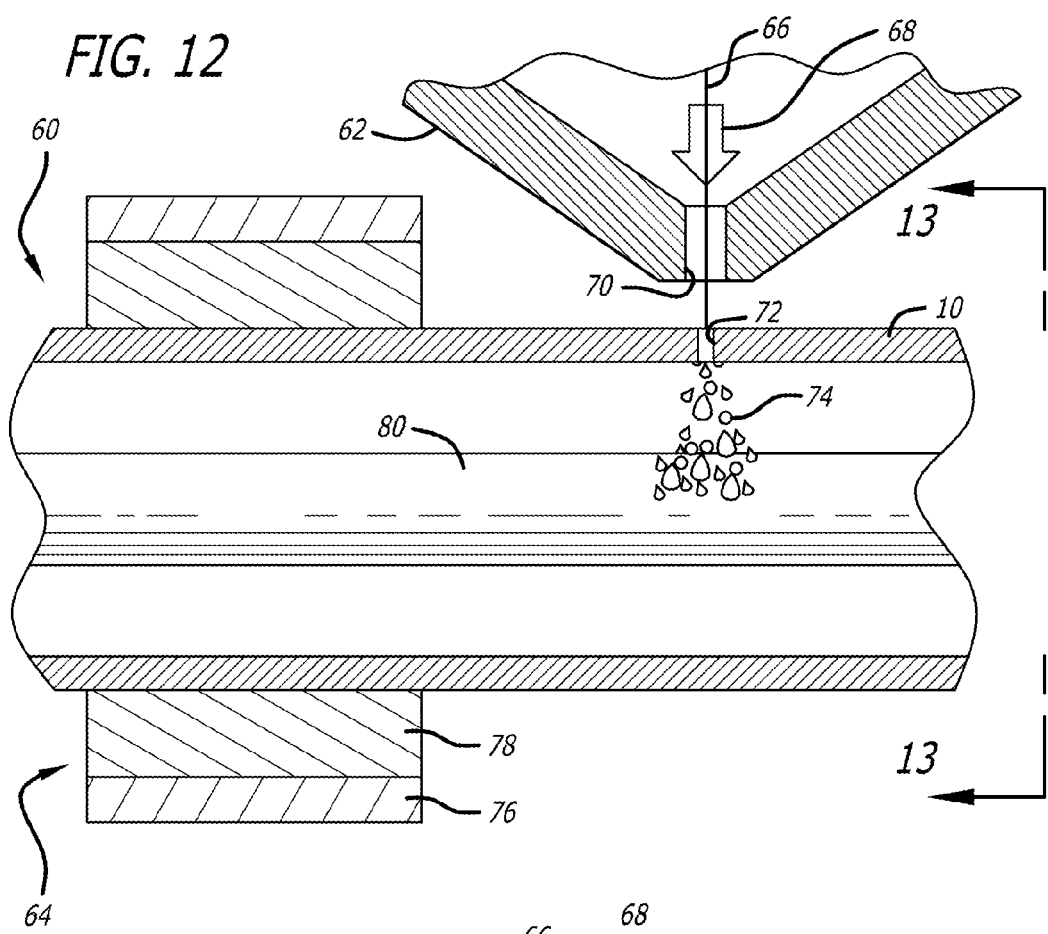
FIG. 12 is a cross-sectional schematic representation showing a system which applies ultrasonic energy to the tubular member during laser cutting.
Figure 13:
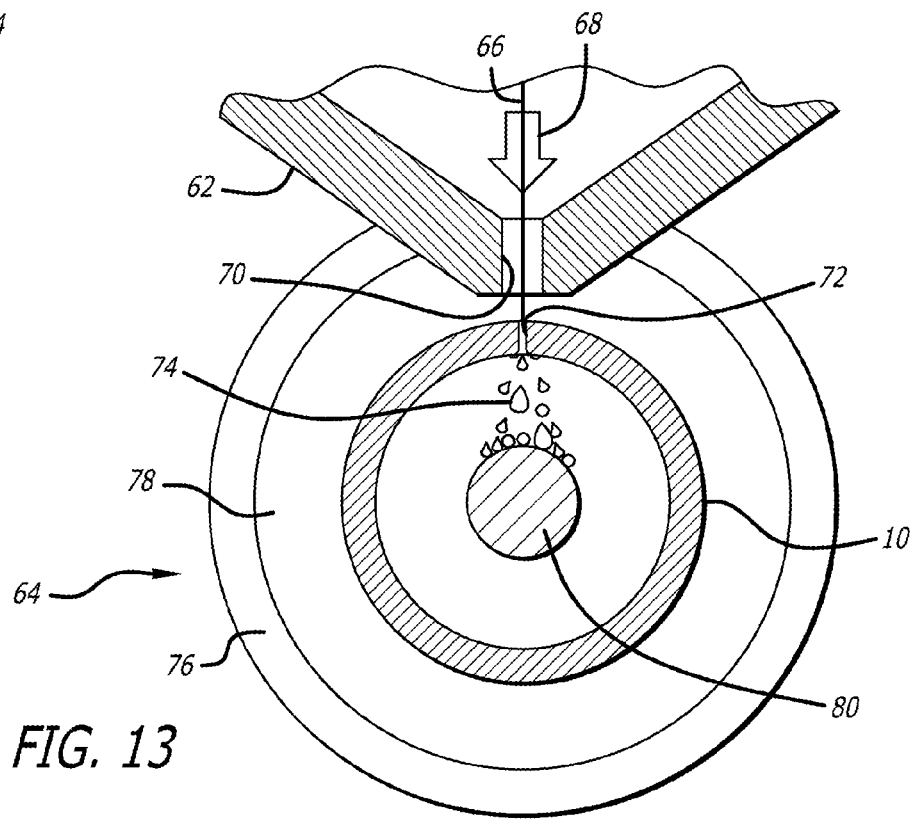
FIG. 13 is a cross-sectional view showing the system of FIG. 12 along line 13-13.

Referring now to FIGS. 12 and 13, another system 60 for dealing with the problems associated with molten slag adhering to the workpiece is disclosed. The system 60 utilizes the application of ultrasonic energy to the tubular member 10 as it is being laser cut to help prevent any slag from solidifying or strongly adhering to an exposed surface of the tubular member. The system 60 includes a laser cutting apparatus 62, shown schematically in the drawing figures, along with an apparatus 64 for applying ultrasonic energy to the tubular member 10 as the tubular member 10 is being laser cut. The ultrasonic apparatus uses high frequency energy to vibrate both the liquidified slag and the tubular member 10 to reduce the ability of the slag to strongly adhere to the exposed portions of the tubular member. When liquids are exposed to these high frequency vibrations, both physical and chemical changes occur as a result of a physical phenomenon, known as cavitation. Cavitation is the formation, expansion, and implosion of microscopic gas bubbles in liquid as the molecules in the liquid absorb ultrasonic energy. If the vibration is sufficiently intense, it should break the attractive forces in the existing molecules of the slag and reduce its ability to bond to a surface.

In this aspect of the present invention, the laser cutting system 60 is shown using a conventional laser cutting apparatus 62 which utilizes air or oxygen to create the slots or kerfs extending through the wall of the tubular member 10. Additionally, the laser cutting apparatus 62 could use pressurized inert gas, such as argon or helium, as is disclosed herein. In accordance with the present invention, still other laser cutting equipment could also be used to cut the tubular member 10.

Generally, as is schematically depicted in FIGS. 12 and 13, a laser beam 66 locally heats the tubular member 10 while the pressurized medium, depicted by arrow 68, is blown through a small coaxial orifice 70 directly onto the heated region in order to create the slots or kerfs 72. During the cutting process, slag 74 will form and will adhere to any exposed surface of the tubular member. The ultrasonic energy apparatus 64 helps to prevent this from occurring by applying ultrasonic energy directly to the tubular member 10, and any generated slag 74, to help prevent the slag from solidifying on any exposed surface of the tubular member 10.

As is shown schematically in FIGS. 12 and 13, the ultrasonic energy generating apparatus 64 includes an ultrasonic transducer 76 which is coupled to a bushing 78. This bushing 78 is, in turn, coupled to the tubular member 10 which will be laser cut by the laser apparatus 62. When subjected to ultrasonic energy, the slag 74 should either harmlessly fall from the surface of the tubular member or should be minimally bonded to the tubular member 10. In other words, the ultrasonic energy will help to prevent the slag 74 from "welding" itself to the surface of the tubular member 10. If the slag 74 becomes only minimally bonded, it should be easier to remove from the surface of the tubular member 10 using, for example, mechanical and/or chemical removal techniques, such as those described above.

The system 60 also utilizes an internal mandrel 80, or other component, which could be placed within the lumen of the tubular member 10 to help catch some of the slag 74 before it hits an exposed surface of the tubular member. The mandrel 80 can be made, for example, from copper. Additionally, in the method and system disclosed in FIGS. 12 and 13, only the tubular member 10 is shown being cut by the laser cutting apparatus 62. It should also be appreciated that a sacrificial mask, made in accordance with the present invention, could also be used with the tubular member 10 to further prevent slag from adhering to the finished workpiece.

The present embodiment shows the ultrasonic energy generating apparatus 64 as a simple transducer/bushing assembly. However, it will be appreciated by those skilled in the art that other structures could be utilized to apply the ultrasonic energy to the tubular member 10 as it is being laser cut without departing from the spirit and scope of the present invention. For these reasons, the present invention is not limited to the ultrasonic energy generating apparatus disclosed in the this particular embodiment.

Referring now to FIGS. 14 and 15, another apparatus which can be used in post-cutting procedures is disclosed. These figures show a compressed air mounting apparatus 90 which can be used to clean the surface of the tubular member 10 of slag and other impurities after the tubular member 10 has been cut. The compressed air mounting apparatus includes a length of tubing 92 having numerous outlet openings 94 which are in fluid communication with the lumen (not shown) of the tubing 92. One end 96 of the tubing 92 is coupled to a fitting 98 which is, in turn, attached to a compressed air supply 100. The other end 102 of the tubing 92 can be closed.

In use, the compressed air supply 100 provides an ample supply of compressed air which shoots out of the outlet openings 94 to create multiple jets of air which strike the surface of the laser-cut tubular member 10, shown mounted on the tubing 92 of the apparatus 90 in FIG. 15. The laser-cut tubular member 10 would be slidable on the tubing 92 so that the jets of air will strike the surface to remove any slag 104 or foreign particles (sometimes referred to as "islands"). The apparatus 90 could be encased within a housing 106 to contain the particles of slag 104 which will be blown off of the workpiece. It should be appreciated that other gases and fluids besides air could be used as the medium for this apparatus 90.

Figure 16:
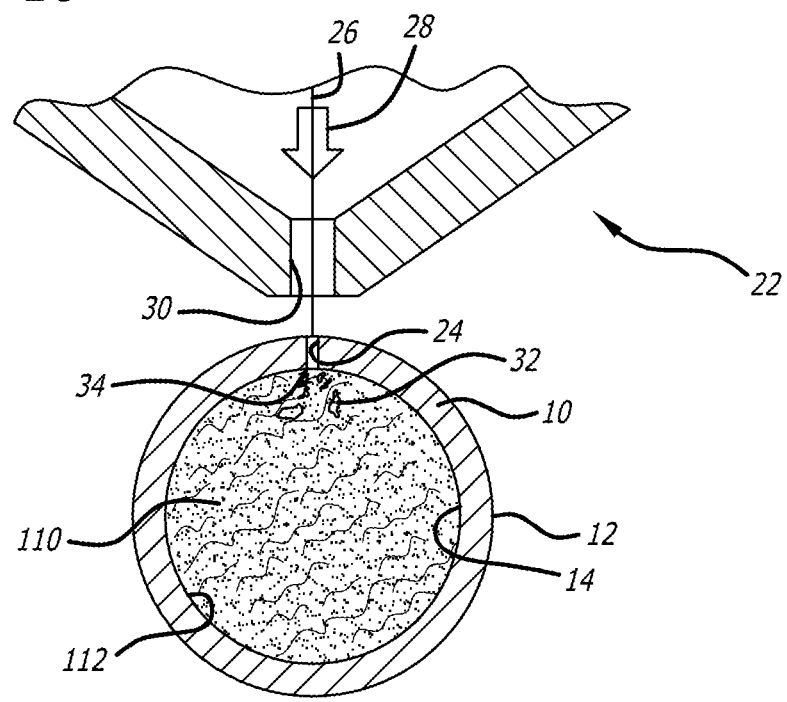
FIG. 16 is a schematic depiction showing a tubular member with a foam insert which reduces stress in the tubular member as a laser cuts one side of the tubular member.
Figure 17:
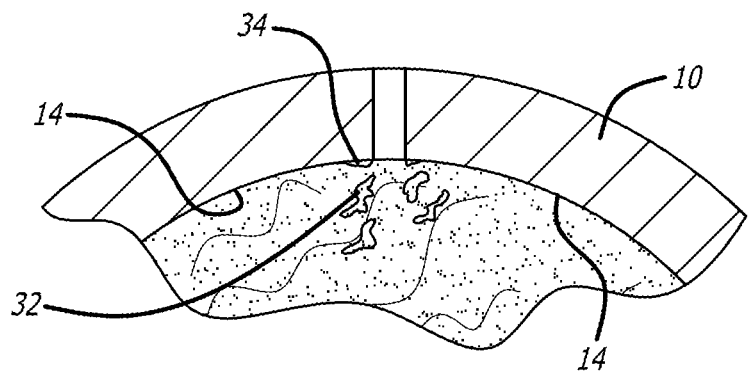
FIG. 17 is a side elevational view showing the foam insert and resulting build up of recast material or "slag" along the bottom edge of the slot or kerf formed on the tubular member.

Referring now to FIGS. 16 and 17, another method for cutting the tubular member 10 is shown. In this particular method, the disposable mask is replaced with a solid sacrificial material in the form of a sacrificial block 110 formed within the lumen 112 of the tubular member 10. This sacrificial block is intended to fill or substantially fill the entire lumen 112 of the tubular member 10 in order to protect the inner surface 14 of the tubular member 10 from the accumulation of recast slag. This sacrificial block 110 can be made from a foam or foam-like material or a resin or resin-like material. Generally, these types of materials are initially in a liquid or semi-solid state and will solidify after a certain period of time or upon application of an agent or other source which transforms the liquid or semi-solid material into a solid structure. In this fashion, the inner lumen 112 can be initially filed with this liquid or semi-solid material which will be allowed to harden to a more solid structure. This solid sacrificial block 110 allows the laser to more accurately cut the tubular member 10 into the desired configuration. This is due to the fact that the solid sacrificial block 110 helps to counter any stresses acting on the tubular member as material is being removed during the laser process. This can be explained as follows. Due to the process by which thin-walled tubular members are manufactured, there are usually residual stresses within the workpiece. Additionally, as patterns are lased into the tubular member, islands or recast slag fall out of the pattern. As the islands fall out of the pattern, they leave behind narrow/thin features that are susceptible to shifting slightly due to both the stresses in the tubing and the fact that the tubing is not directly supported in the lasing zone. When the tubing shifts slightly in this manner, the pattern lased into the tubing may become somewhat distorted, since precision lasing of the remaining portion of the tubing will be slightly shifted as well. As a result, the finished workpiece may include defects which renders the workpiece unusable.

In the current method, the use of foam, resin or alternative materials provides the tubular member with an inner "support" which helps to prevent this slight shifting of the tubing as it gets laser cut. Again, the method includes filling at least a portion of the lumen of the tubular member 10 with a removable sacrificial material in the form of a sacrificial block 110 which can be initially in a non-solid state, i.e., a liquid or semi-solid state. This sacrificial material is then allowed to harden within the lumen of the tubular member. The lasing process can then continue such that portions of the tubular member are selectively removed using the laser device. Again, the sacrificial block 110 acts to stabilize the tubular member 10 as it is being cut, especially the narrow and often intricate strut patterns which are lased into the tubular member 10. Recast slag 32 will be trapped within the sacrificial block 110 for later removal. Recast droplets 34 which form on the inner surface 14 will be trapped as well. The presence of this sacrificial block 110 will prevent recast slag 32 from striking and adhering to the opposite surface of the tubular member. Thereafter, the hardened sacrificial block 110 can be removed from the lumen of the tubular member.

The sacrificial block 110 can be removed by any one of a number of ways. For example, the block 110 can be chemically etched away or mechanically removed. The chemical and mechanical processes described herein could be used to remove the solid sacrificial block 110 from the tubular member 10.

Suitable foams which can be used in this method include polyurethane-based and viscoelastic (memory) foams. Suitable resins include polyester and urethane casting resins. Other alternative materials include silicone rubber. Any materials used would be required to meet certain flammability and fume-release thresholds.

Figure 18:
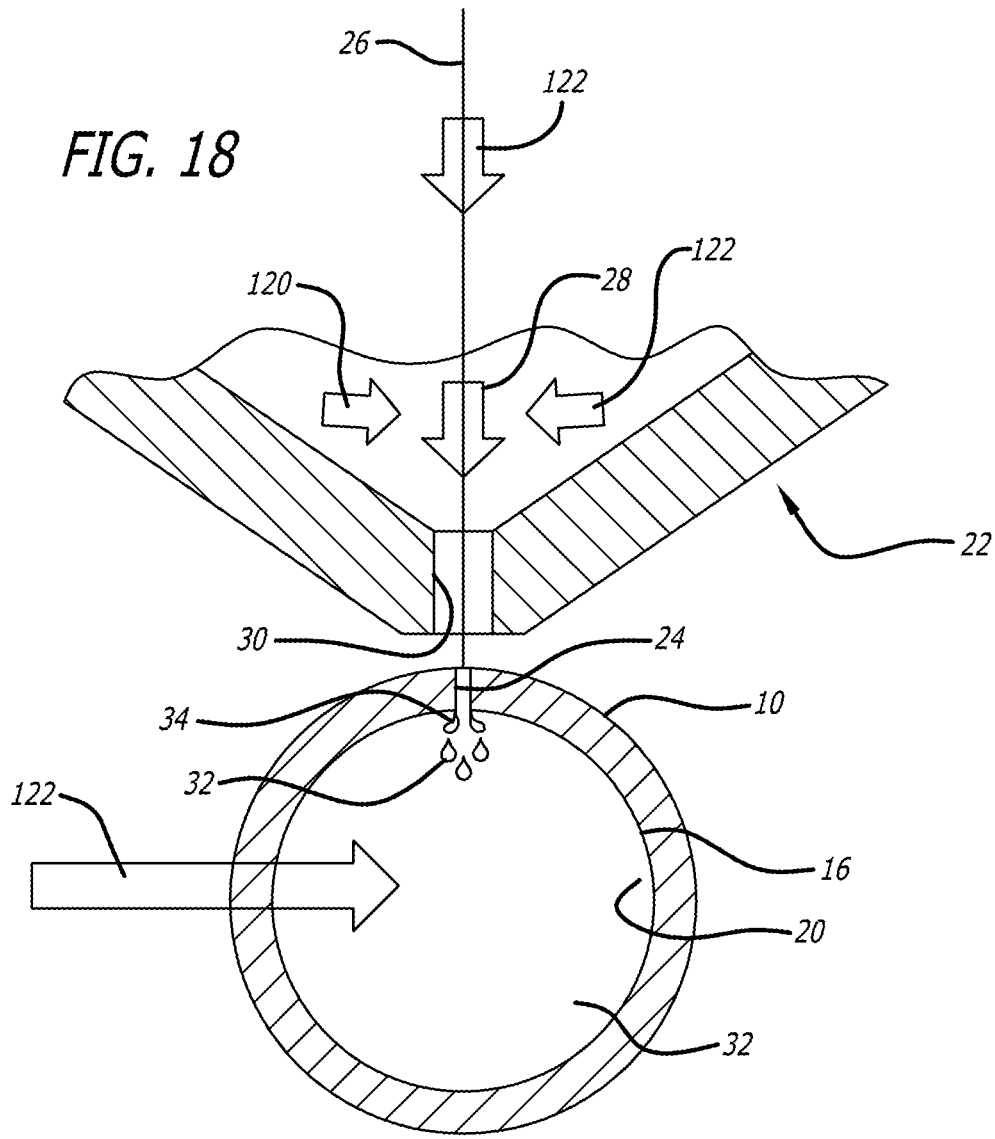
FIG. 18 is a schematic depiction of another embodiment of the present invention which utilizes a secondary gas, a powder or a gas mixture during laser cutting of the tubular member to cause the recast slag to become more brittle for easy removal from the workpiece

Referring now to FIG. 18, another method for forming a device from a tubular member is disclosed. In this particular method, the invention is directed to the formation of recast material or slag which is more brittle than slag which is normally generated during conventional laser processing. Since more brittle slag is much easier to remove in post polishing and removal steps, the overall manufacturing process can become more efficient and economical. This process can be implemented for any laser cutting method in which removal of slag is required. It is particularly applicable to laser cutting of Nickel-Titanium alloys that include more challenging post-processing cleaning steps which need to be performed on the cut workpiece.

In one preferred embodiment of the present invention, the laser cutting process is modified in order to produce a more brittle slag. Referring to FIG. 18, the assist gas 28, sometimes referred to as a "shielding gas," used to remove molten material from the laser cutting site can be modified as to its purity. The present invention seeks to increase the brittleness of the produced slag droplets 34 by decreasing the purity of the shielding gas 28 below a threshold level that will still permit effective shielding and slag removal from the cutting site while ensuring that the impurities of the gas react with the melted material to form "intermetallics" that preferably embrittle the resulting slag material.

Once the slag is embrittled, it can be more easily removed using, for example, mechanical polishing techniques, such as bead blasting and honing. In one particular example, the shielding gas 28 can be Argon and the purity of the shielding gas 28 can be reduced below a threshold of about 99.9998% Argon in order to embrittle the resulting slag. In doing so, the Argon gas can be decreased from "spectra grade" Argon to "Research" or "UHP" grades of Argon, which range from about 99.9995 to 99.9998% pure Argon. Other gases may have different thresholds for affecting the brittleness of the resulting slag. For example, Helium gas may be used for the shielding gas. Helium comes in both "Research" and "UHP" grades, with purity levels around 99.9999 to 99.999% Helium. Suitable thresholds can be selected for various alternative non-combustible gases without undue experimentation.

Another method for forming brittle slag includes the adding of gaseous impurities to the shielding gas 28. For example, suitable powders 120 can be mixed with the shielding gas 28 to form an aerosol. Suitable powders 120 include materials which will create intermetallics when combined with the material make up of the tubular member 10. For example, powder materials which include carbon and alumina are suitable when the tubular member is made from Nickel-Titanium alloys. In this particular method, the melted portion of the tubular member 10 becomes "doped" with a material (the added powder) which helps to create a more brittle slag.

In yet another alternative method, a separate secondary gas 122 or gas/powder mixture may be directed to the flow of shielding gas 28. For example, the secondary gas 122 may be a lower grade of Argon or even another gas which may be simultaneously directed to the shielding gas 28. Such secondary gas can be directed, for example, through the lumen 112 of the tubular member 10, as is shown in FIG. 18. This secondary gas also may include powder(s) which can form intermetallics which attain a more brittle slag. This secondary gas or gas mixture can be, for example, directed in parallel with, or perpendicular to, the shielding gas 28. This particular method may be advantageous since it may also help to prevent the embrittlement of the resulting workpiece. In this aspect of the invention, only the recast slag droplets 34 would be affected by this secondary gas, resulting in a stronger workpiece. A sacrificial mask (not shown in FIG. 18) could also be utilized with the above-identified methods to help prevent recast slag from striking and adhering to the inner surface of the tubular member during lasing. Such a sacrificial mask could be removed using any of the removal methods described herein.

In an alternative embodiment, shown in FIGS. 19 and 20, the consistency of the slag may be modified through the use of a composite tubular member 10 with a sacrificial inner layer 124 for doping the slag as it recasts. In one embodiment, the composite tubular member 10 may comprise an outer layer of the material intended for the final product, e.g. stainless steel or Nitinol. The sacrificial inner layer 124 may be deposited on the tubular member 10 using a number of known manufacturing techniques such as co-extrusion, composite drawing, or even through spray coating the inner surface of the tubular member. The inner layer 124 may be formed as a sleeve which is placed within the lumen 112 of the tubular member 10. Materials that are contemplated for this inner sacrificial layer include, but are limited to, metals such as alumina, as well as polymers such as polyamides, polyurethanes, silicone modified polyurethanes, fluoropolymers, polyolefins, polyimides, polyintines, (methyl)acrylic polymers, polyesters, polyglycolide, polyglycolide (PGA), poly(Llactide) (PLLA), poly(D,L-lactide) (PDLLA), poly(L-lactide-co-glycolide) (PLGA), poly(D,L-lactide-coglycolide) (PDLGA), poly(e-caprolactone) (PCL), polydioxanone, poly(ethylene glycol) (PEG), poly(vinyl alcohol), and co-polymers thereof, to name a few.

The effect of the inner sacrificial liner 124 is described as follows. The laser melts the tubular member 10 and sacrificial inner liner 124 forming a molten material which is blown through the tubular member 10 by the laser assist gas. The molten material of the tubular member 10 will combine with the material forming the sacrificial inner liner 124 to form a slag with a select intermetallic composition. This intermetallic composition will increase the brittleness of the bulk slag, thereby making removal of the slag much easier from the workpiece in post-processing steps. For example, Nitinol tubing can be used as the tubular member and alumina could be use as the sacrificial inner liner. The melted Nitinol and alumina would combine to partially form a Ti—Al intermetallic, which would be less ductile and less fracture resistant, in accordance with this invention.

An alternative embodiment of the present invention can utilize a tubular member formed from Nickel-Titanium or a Nickel-Titanium alloy and copper as the sacrificial inner layer. The melting of the tubular member may result in a slag having inclusions of NiTiCu, which is more brittle than slag made simply from Nickel-Titanium. These inclusions will become brittle when formed at about 10% Cu, which will create more easily removable slag in accordance with this invention.

In an alternative embodiment, the inner sacrificial liner 124 need not be a consistent tubing or sleeve as shown in FIGS. 19 and 20, but may be formed by spray coating, which should yield the necessary material to result in the modified slag consistency during laser cutting. For example, a coating of powder alumina may be disposed on the inner surface of the stent tubing. In this embodiment, the laser cutting is not anticipated to heat the alumina beyond its melting point but, as the tubular member is melted and displaced by the laser assist gas, it would combine with the alumina particulates forming a recast slag that contains stress risers that are more brittle and easier to remove.

Figure 21:
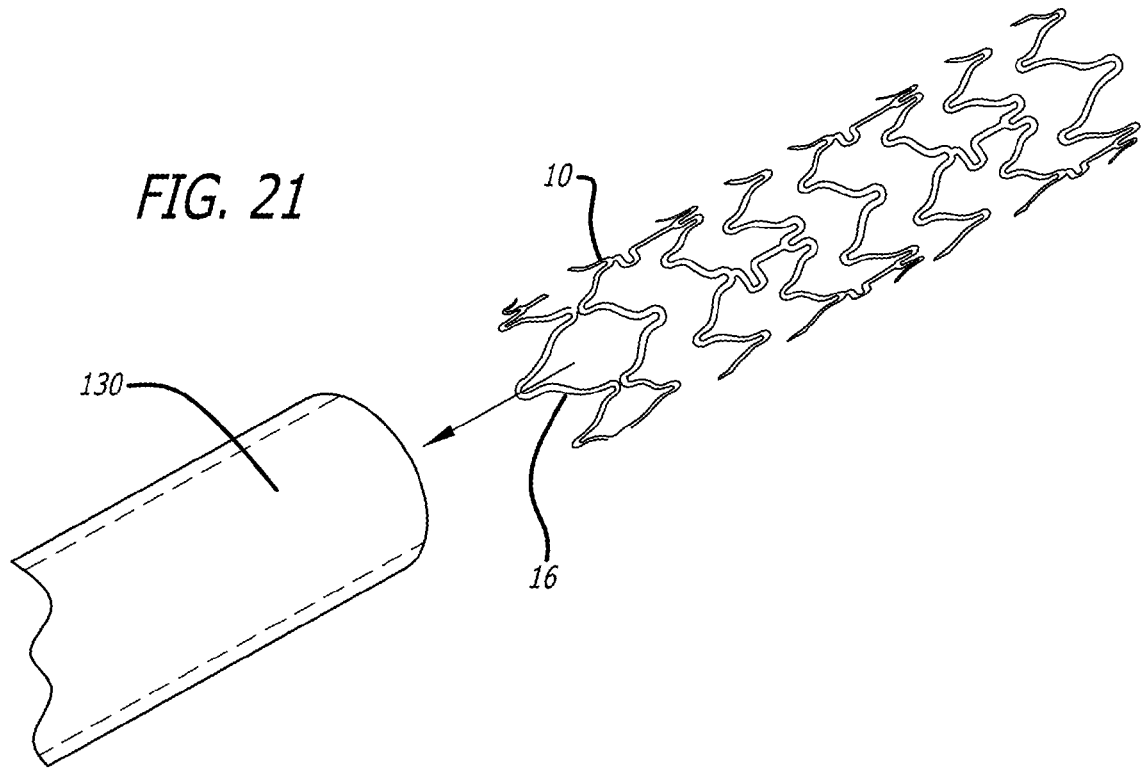
FIG. 21 is a perspective view showing a workpiece (lased tubular member and sacrificial sleeve) being placed into a fixture for holding the workpiece during a reaming operation.
Figure 22:
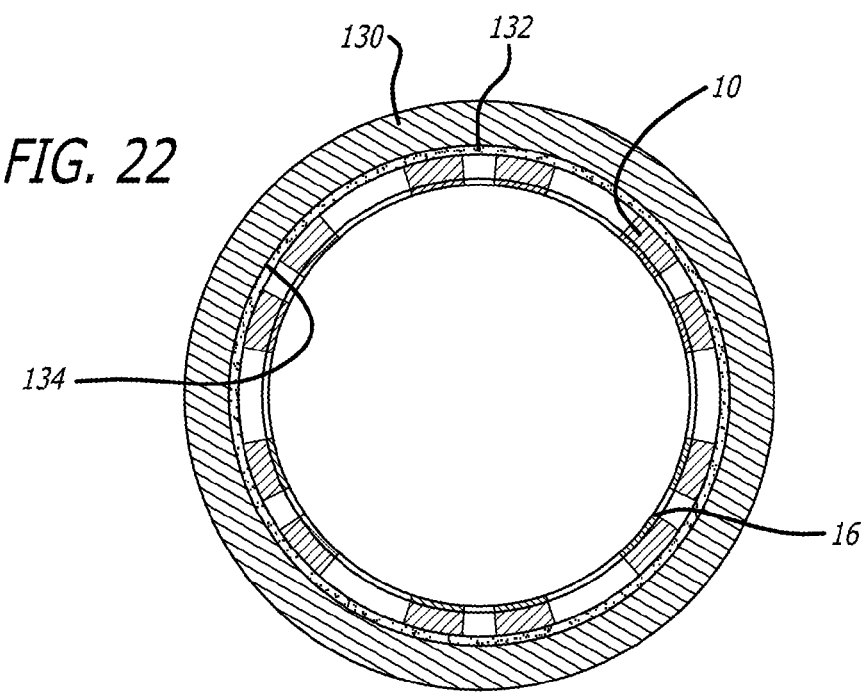
FIG. 22 is a cross sectional view showing the workpiece of FIG. 21 placed within the fixture of FIG. 21.

Referring now to FIGS. 21 and 22, an alternative method is shown for post-processing of the laser cut workpiece. As can be seen in FIG. 21, the tubular member 10 and sacrificial sleeve 16 have been cut by a laser source to form a workpiece which needs additional processing in order to remove the remaining portions of the sacrificial sleeve 16 which remains affixed to the inner surface of the cut tubular member 10. In the present embodiment, the sacrificial sleeve 16 is removed by drilling or reaming the material off of the inner surface of the workpiece. Accordingly, it can be difficult to do such an operation absent a structure which holds the workpiece during reaming. FIG. 21 shows a fixture 130 which can be used to hold the workpiece. The fixture 130 can simply be a length of tubing which is larger than the workpiece. The fixture 130 can be made to create a slip fit between the outer diameter of the workpiece and the inner diameter of the fixture. The outer surface 12 of the workpiece can be initially bonded, via an adhesive 132, to the inner surface 134 of the fixture 130. This prevents the workpiece from twisting during the drilling/reaming process. The workpiece can then be drilled/reamed to remove the remaining portions of the sacrificial sleeve 16 which remains affixed to the inner surface of the workpiece.

After removal of this sleeve 16, the workpiece now needs to be removed from the fixture 130 without damaging the workpiece.

The removal of the workpiece from the fixture will depend upon the material used for the fixture 130. For example, if aluminum tubing is used to create the fixture 130, then the assembly (both the fixture and workpiece) can be initially heated, quenched and subjected to ultrasonic vibration to separate the workpiece from the fixture. This process effectively allows the workpiece to slip freely from the aluminum fixture. For example, the assembly can be initially heated in a molten salt bath. Such a bath can have a temperature approximately 500 to 530° C. The assembly can be heated for approximately 2 minutes. Thereafter, the assembly can be water quenched to reduce its temperature and transferred to a hot 80° C. water bath where the assembly can then be subjected to ultrasonic vibrations for about 30 minutes. This processing allows the workpiece to freely slide out of the fixture.

In an alternative embodiment, the fixture can be made from stainless steel (SS). The workpiece can be likewise glued or bonded into place on the inner surface of the fixture. The workpiece can then be removed by placing the assembly into a hot acid solution which aggressively attacks the stainless steel fixture but does not etch the Nickel-titanium workpiece. The acid solution can be, for example, Nitric, Sulfuric and HCL acids. The acid solution should be sufficiently strong to break the bond of the glue used to bond the workpiece to the fixture. In a short time, about 1 minute, the workpiece will become free from its bond with the stainless steel fixture.

A suitable glue for bonding the workpiece to the aluminum or stainless steel fixture is Cyanoacrylate, the generic name for cyanoacrylate based fast-acting glues such as methyl 2-cyranoacrylate, ethyl-2-cyanoacrylate (commonly sold under trade names like Super Glue® and Krazy Glue®.

Referring now to FIGS. 23 to 26, another method of manufacturing a workpiece utilizing a sacrificial mask is disclosed. Again, it should be appreciated that the use of a sacrificial mask eliminates much post-processing of the workpiece. However, if there is a small gap between the sacrificial mask (sleeve 16) and the tubular member 10, it is possible for some slag built up to accumulate. As mentioned above, this slag build up, often referred to as a slag lip, is often difficult to remove from a cut workpiece. Therefore, it can be beneficial to eliminate all or as much as possible of the gap formed between the tubular member 10 and sacrificial sleeve 16.

FIGS. 23 to 26 depict a method which can greatly eliminate any gap formed between the tubular member 10 and the sacrificial sleeve 16. This aspect of the invention utilizes the self-expanding properties of Nickel-Titanium alloy to create a virtually gap free assembly. The invention is directed to a method of placing the nickel-titanium tubular member over a slightly oversized sacrificial sleeve. For example, if the inner diameter of the tubular member is 0.050," then the sacrificial sleeve should have an outer diameter which is slightly larger than 0.050".

Figure 23:
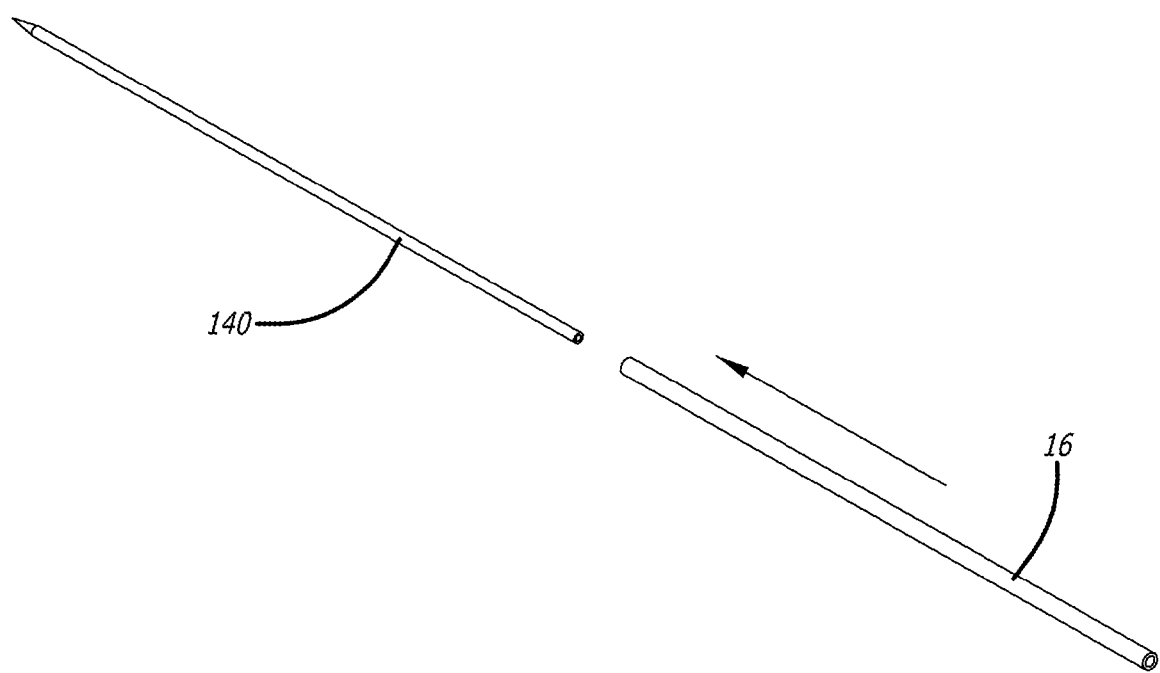
FIG. 23 is a perspective view of a tubular disposable mask being inserted over a hollow mandrel.
Figure 24:
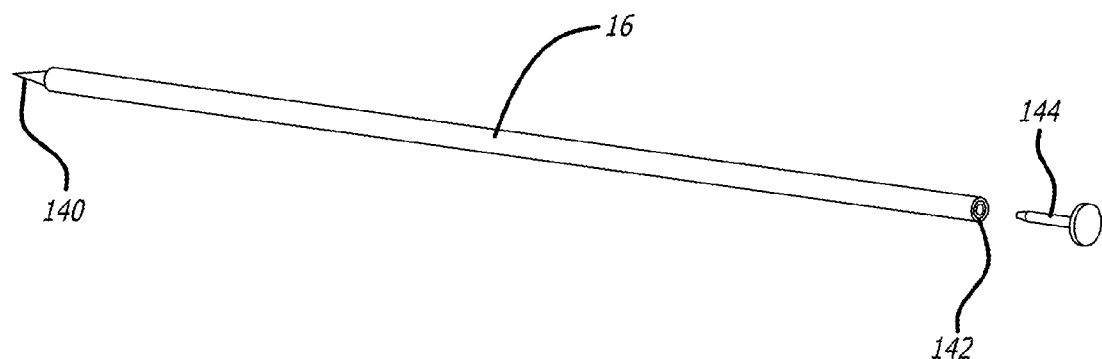
FIG. 24 is a perspective view of a pin being inserted into the mandrel shown in FIG. 23.
Figure 25:
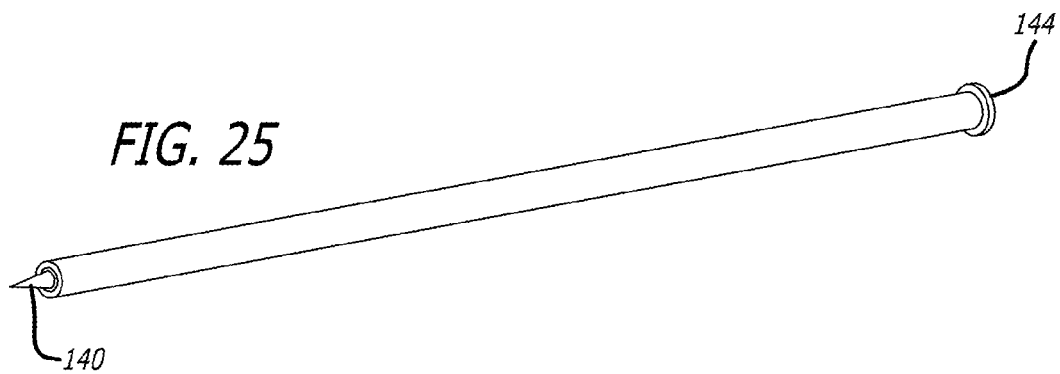
FIG. 25 is a perspective view of a tubular member being inserted over the assembly shown in FIG. 24.
Figure 26:
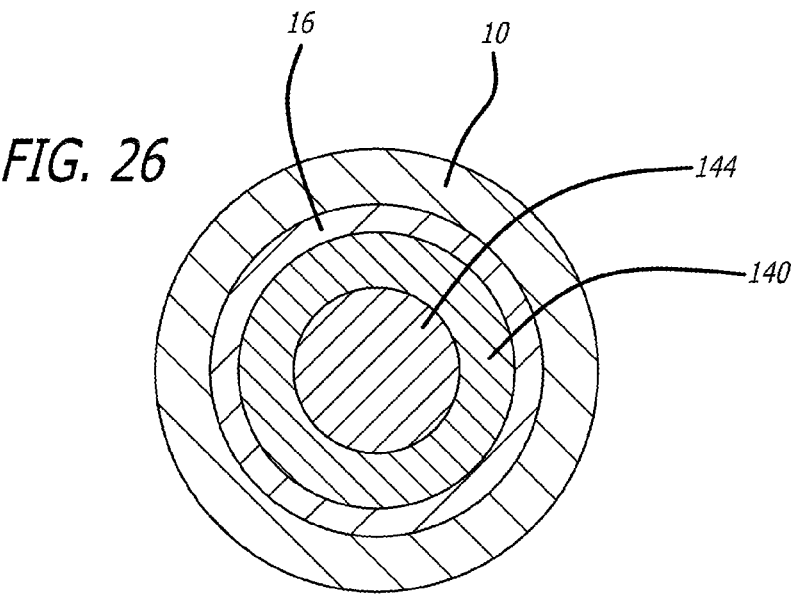
FIG. 26 is a cross-section view taken along line 26-26.

Initially, as can be seen in FIG. 23, an oversized sacrificial sleeve 16 is initially placed over a mandrel 140 which can include an inner lumen 142. A pin 144 can be placed within this lumen 142 to later assist in the removal of the mandrel 140 from the sacrificial sleeve 16. The tubular member 10, which is made from nickel-titanium alloy or similar self-expanding material, can then be transformed from its austinitic phase to its martensitic phase by cooling the tubular member 10 using techniques well known in the art. The tubular member 10 would be cooled down to a temperature below its AF temperature. Once in its martensitic state, the tubular member 10 will be much softer and will allow the slightly oversized sacrificial sleeve to be placed within its inner lumen (see FIG. 25). The pin 144 and mandrel 140 can then be removed once the tubular member 10 is properly placed over the sacrificial sleeve 16. The tubular member 10 can then be brought back to its austinitic phase by heating the tubular member to a high temperature, for example, room temperature. During transformation from the cooler martensitic state to the austenitic state, the tubular member 10 will begin to shrink back to its initial diameter, which will create a very tight fit over the sacrificial sleeve. As a result, the tubular member 10 will be tightly encased over the oversized sacrificial sleeve resulting in virtually no gap between these two components. The tubular member 10 and sacrificial sleeve 16 can now be lased to the desired pattern.

Figure 27:
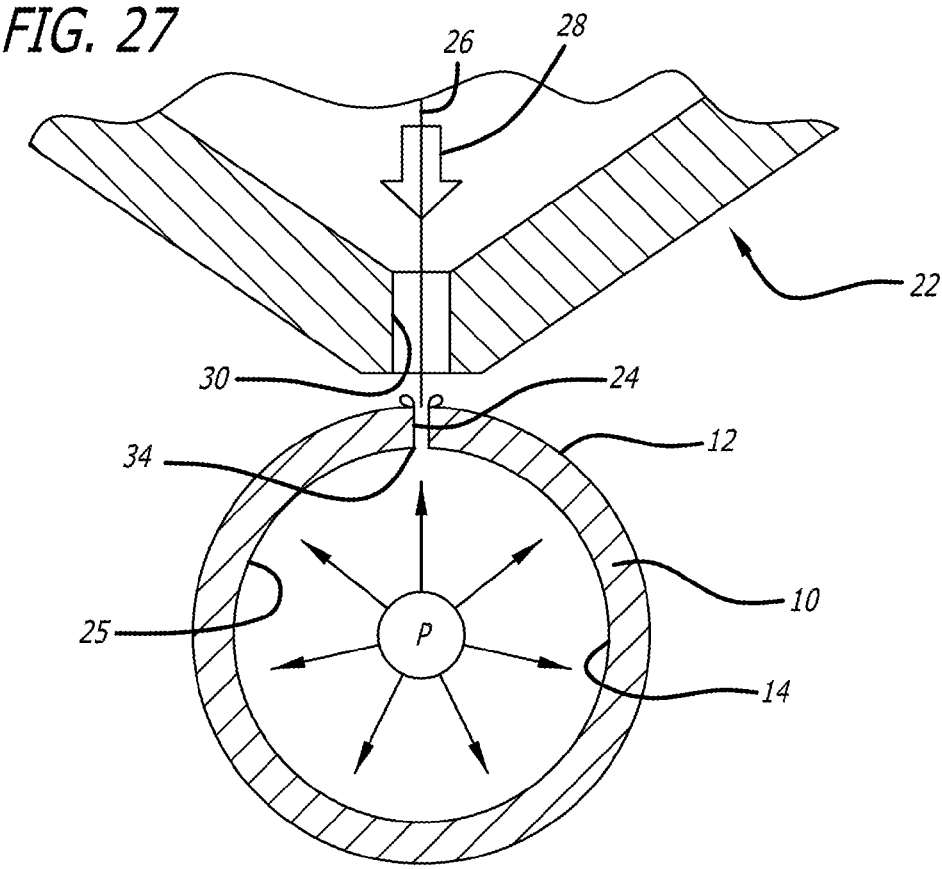
FIG. 27 is a schematic representation of a system made in accordance with the present invention showing a pressurized tubular member being laser cut into a workpiece.
Figure 28:
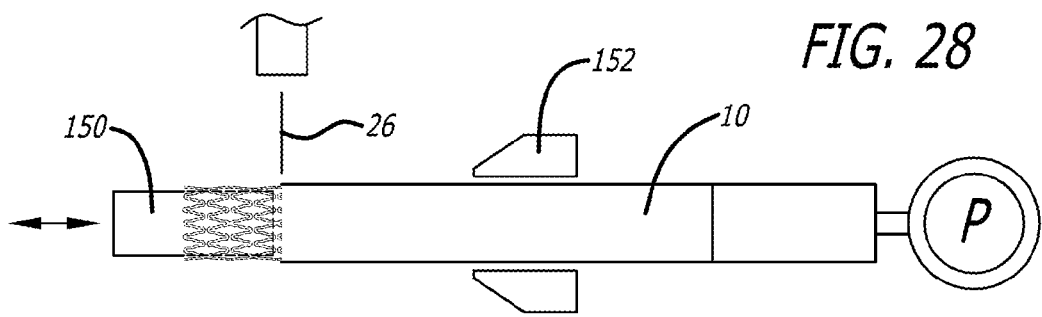
FIG. 28 is a schematic representation of the system disclosed in FIG. 27 for making a device, such as a stent, from a tubular member using a laser device and pressurized gas which causes resulting slag to develop on the outside of the tubular member.
Figure 29:
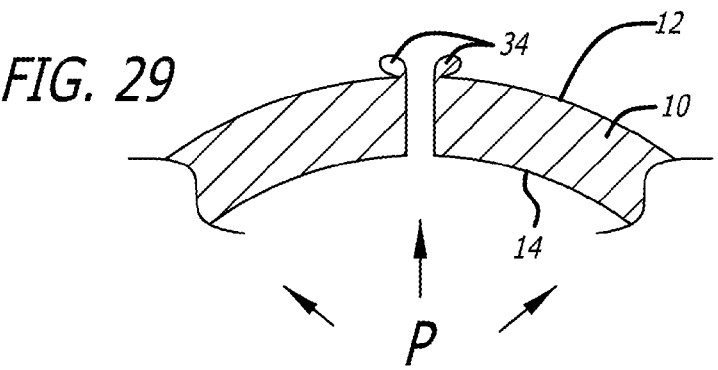
FIG. 29 is a cross sectional view showing the tubular member cut in accordance with FIGS. 20 and 21 in which the recast material is formed on the outer surface of the disposable mask.
Figure 37:
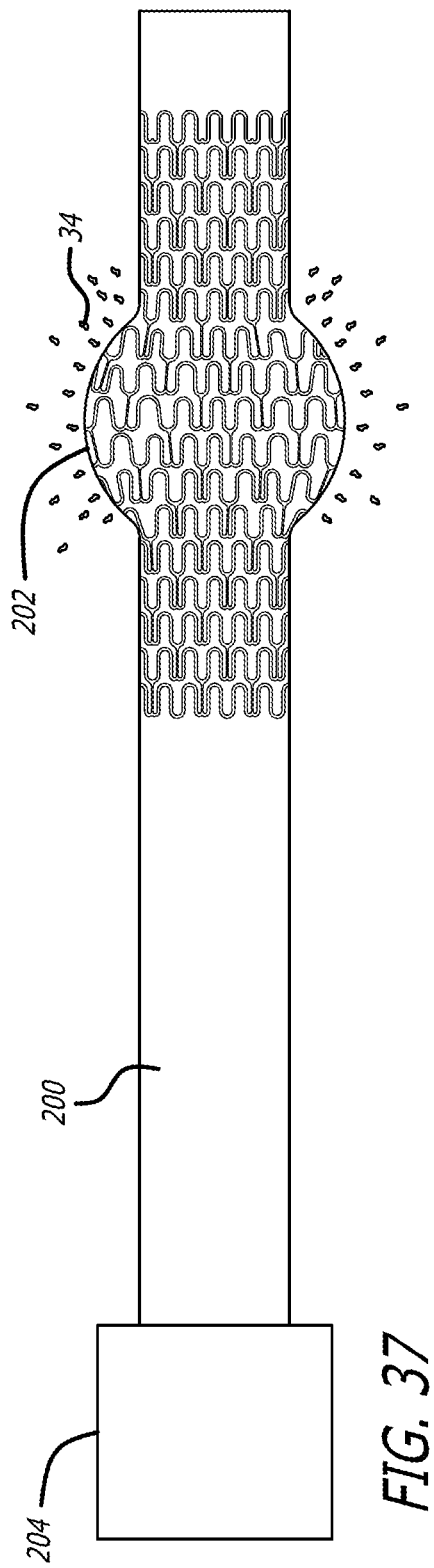
FIG. 37 is a perspective view of another embodiment of a mandrel with an enlarged diameter made in accordance with the present invention.
Figure 38:
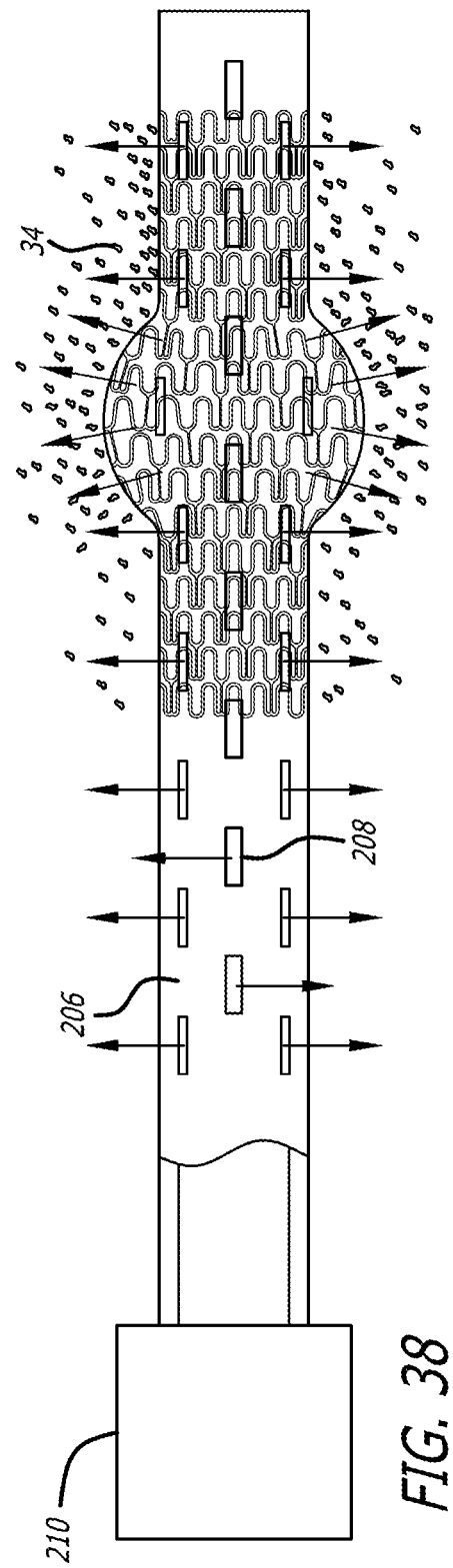
FIG. 38 is a view of the surface of an embodiment of a pressurized mandrel made in accordance with the present invention.

Referring now to FIGS. 27 to 29, another method and system for reducing the amount of slag distributed on a tubing inner diameter during laser cutting is depicted. In this particular invention, during laser cutting, the inner lumen of the tubular member 10 is pressurized by a gas or liquid. As the laser beam cuts through the tubing wall, the pressurized medium will force the melted material toward the outer surface of the tubular member 10 against the directional force created by the laser and laser shielding gas. Therefore, the inner lumen of the tubular member will remain relatively clean as the slag is redistributed away from it.

Referring specifically to FIG. 28, this invention can utilize, for example, standard laser cutting equipment in which a collet and various actuation mechanism are used to grip, rotate, and advance the tubular member 10. The laser source 26 is generally directed perpendicular to the cutting surface and toward the inner diameter of the tubular member 10. A pressure source P is coupled with the equipment used to cut the tubular member 10. The set up is generally shown schematically in FIG. 28. For example, the pressure may be generated using a compressed gas source. It is preferred that the gas be a non-volatile or non-flammable gas. Alternatively, the pressurized gas could be specially selected in order to create the intermetallics in the recast slag as is described above. For example, the pressurized gas may be a lower grade Argon gas or other gas which acts with the molten material to form more brittle slag. This pressurized gas could also include powder(s) which also can help to form intermetallics that create more brittle slag.

The pressurized gas may be regulated to a desirable pressure before entering the tubular member. An appropriate regulation pressure would be higher than the pressure placed on the melted stent tubing by the laser and laser shielding gas.

In utilizing such a pressurized system, it should be recognized that there will be a drop in pressure as the number of slots or openings are lased into the tubular member. In one particular embodiment of the present invention, as depicted in FIG. 28, the end of the tubular member 10 may be plugged using a movable plug 150 which is designed to reduce the amount of the pressurized medium that is lost through the openings cut into the tubular member. This plug 150 helps to ensure that the tubular member will remain properly pressurized during laser cutting. It is possible to implement a mechanism (not shown) which moves the plug 150 within the tubular member as the laser cutting process proceeds. In this fashion, such an arrangement will allow the mandrel to fill in the areas which have been lased to ensure that minimal area exists for the pressurized gas to escape. For example, the plug 150 may be a movable rod with an end that remains just distal to the laser relative to the pressurized end. As the tubular member is being cut with the desired pattern, the plug 150 would also move with the tubular member to seal the area of the tubular member which has been laser cut in order to reduce the amount of pressurized medium which will escape. While this moving plug will not "plug" or seal all of the open areas, it will help to minimize the area where pressurized medium can escape. This will ensure that the areas near the laser cutting site is sufficiently supplied with pressurized medium to force the melted slag toward the outer surface of the tubular member.

FIG. 29 illustrates a cut tube in which the pressurized medium has redistributed the slag toward the outer surface 12 of the tubular member 10. The formation of the slag 34 along the outer surface of the tubular member makes its removal much easier than if the slag is formed within the lumen of the tubular member. It permits the use of grinding processes that are otherwise difficult to use within the lumen. Also, electropolishing processes and descaling processes are improved since the required chemicals and solutions are more easily placed along the outer tubing wall and can also be circulated more easily in that area.

Referring now to FIGS. 30 to 36, a system and method for reducing the formation of slag on the inner surface of the tubular member is schematically depicted. FIG. 30 shows a honing mandrel 160 attached to a variable speed motor 162. This honing mandrel 162 is designed to rotate while the tubular member 10 is being laser cut. Even though the honing mandrel 160 is being struck by the laser beam, it was not getting burnt or welded into place since it is designed to rotate during the laser cutting operation.

As can seen in FIG. 30, a laser source 26 is schematically depicted cutting the tubular member 10. The honing mandrel 160 is shown extending through the inner lumen. As can be seen, the mandrel 160 blocks slag build up on the inner surface 14 of the tubular member 10. The rotating mandrel also may include a surface portion which contacts, or is very close to making contact with, the inner surface of the tubular member. In this regard, this portion of the mandrel 160 will "scrape" or "hone" the inner surface of the tubular member as the tubular member is being cut, thus removing molten material as it is being created. FIG. 30 shows a schematic representation which includes a servo motor 164 used to move the tubular member 10 relative to the laser source 26. collets are used to support the tubular member 10. The system may include a gas souse, such as argon gas, which is used as a secondary gas, as is shown in FIG. 30. The use of this secondary gas will assure that no oxygen will contaminate the melt zone. Additional gas flow can be utilized to speed up the cooling rate which will reduce the HAZ (Heat Affected Zone). Since titanium is very difficult to remove from the workpiece, it is important to prevent oxygen from forming titanium oxide. Also, a smaller HAZ means less material to remove in subsequent processing. Additionally, gas pressurization may assist in the remove of slag as it cools. This will help prevent it from building up in the cutting region. Gas can be delivered from the end of the tube or from a bath that completely submerges the laser cutting area. The current system could also employ the use of an ultrasonic source, such as is shown in FIGS. 12 and 13, which should help prevent build up as well.

The honing mandrel 160 can be made from a rod or rod-like member having a substantially uniform outer diameter. Alternatively, a honing segment 168 can be attached to the mandrel 160 via a fastener 172 as is shown in FIG. 31.

The honing mandrel 160 or honing segment 168 can have any one of a number of cross-sectional shapes to aid in the slag removal. For example, the honing mandrel or honing segment 168 may have a round configuration 174 (FIG. 32), a flat with square ends 176 (FIG. 33), a hexagonal shape 178

(FIG. 34), an oval shape 180 (FIG. 34), a flat shape with round ends, triangular, square, brush, fluted or fluted with chip breakers. For example, the mandrel 160 can be made from a solid piece of material, a flexible solid wire or a braided wire. Material which can be used to create the mandrel include, but are not limited to, steel, stainless steel, copper, aluminum, beryllium copper, titanium, titanium/platinum alloy. The outer surface of the honing mandrel 160 and the honing segment 168 may include an abrasive material 170 which helps to scrape the molten material from the inner surface of the lumen. Such materials include, but are not limited to, abrasive coatings such as diamond, cubic boric nitride, plastics, glass and ceramics. The honing mandrel 160 and honing segment 168 may have a surface in which a groove or channel 186 is formed to act as a collection area for the recast material. In one particular embodiment, the channel of groove 186 can be spiral in shape and extend along the length of the mandrel 160 to create a collection area which allows the recast material to "flow" along this channel to the end on the mandrel where the material will be discharged from the inner lumen of the tubular member. Thus, build up of recast material within the inner lumen can be greatly reduced.

In another aspect of the present invention, cleaning and polishing of the cut workpiece can be accomplished by utilizing a mandrel 200 which is capable of aiding in the removal or built-up slag or islands without application of excessive forces which could otherwise damage the often intricately cut workpiece. In this aspect, the cut workpiece could be placed on the mandrel 200 which includes one or more enlarged diameter sections 202. The cut workpiece could be slid over the enlarged diameter section 202 which causes the workpiece to expand slightly within its elastic deformation range. Due to the minimal strains within the workpiece, it is expected that the workpiece will recover substantially to its original diameter. During expansion over the enlarged diameter section of the mandrel, the workpiece will undergo a physical separation from the slag or islands which may still be present on the cut workpiece. As the enlarged diameter section 202 of the mandrel 200 places a radial load on the workpiece and the islands, the islands will tend to dislodge from the workpiece and will be ejected from the pattern of the workpiece. Thus, as the workpiece reverts back to its normal diameter, there will be no, or significantly fewer islands remaining on the workpiece. An alternative mandrel can be made with a number of enlarged diameter sections which causes the workpiece to expand and contract as it moves along the mandrel. The enlarged diameter section can be made in various sizes (diameters and longitudinal lengths) and shapes (example, spherical, conical, irregular, etc). The mandrel could also be coupled to a source 204, such as, for example, an ultrasonic, rotating and or lubricating source which helps to break up the islands formed on the workpiece. Alternatively, the surface of the mandrel could be coated with an abrasive material which hones or grinds the inner surface of the workpiece.

An alternative mandrel 206 with at least one enlarged diameter section(s) 202 could be created from a tubular member which has a central lumen that delivers a pressurized medium, such as gases or fluids, through openings 208 formed on the mandrel to help "blast" islands from the workpiece. Such a mandrel 206 also could be coupled to a source 210 which provides, for example, ultrasonic, rotating, lubrication, to help to break up the islands formed on the workpiece. Alternatively, the surface of this mandrel 206 also could be coated with an abrasive material which hones or grinds the inner surface of the workpiece. As a result, a greater yield of finished workpieces can be accomplished in less time than is normally needed to remove the slag or islands using other manual techniques.

In accordance with the present invention, the laser cutting operation can be performed using machine-controlled laser cutting systems such as those shown in U.S. Pat. No. 5,780,807 to Saunders and U.S. Pat. No. 6,927,359 to Kleine et al, both of which are incorporated by reference herein in their entirety. Such machine-controlled equipment may be required to be modified somewhat to incorporate the machine features of the present invention.

It will be apparent from the foregoing that the present invention provides a new and improved method and apparatus for cutting of metal stents, enabling greater precision, reliability, structural integrity and overall quality, while reducing post-cutting processing and reducing burrs, slag or other imperfections which might otherwise hamper stent integrity and performance. While the invention has been illustrated and described herein in terms of its use in manufacturing an intravascular stent for use in arteries and veins, it will be apparent to those skilled in the art that the invention can be used to manufacture stents for other uses, such as the biliary tract, or to expand prostatic urethras in cases of prostate hyperplasia, and to manufacture other medical products, such as embolic protection devices, requiring precision micromachining.

Therefore, while particular forms of the invention have been illustrated and described, various modifications can be made without departing from the spirit and scope of the invention. Accordingly, it is not intended that the invention be limited, except as by the appended claims.

We claim:

1. A method for making a device, the method comprising:
providing a tubular member with an inner lumen which will be formed into the device;
placing a removable sacrificial material on the inner surface of the tubular member;
selectively removing a portion of the tubular member and sacrificial material;
attaching the outer surface of the tubular member to the inner surface of a fixture;
reaming the sacrificial material from the lumen of the tubular member; and
heating the tubular member and the fixture.

2. The method of claim 1, wherein the heating of the tubular member and tubular fixture is performed by subjecting the components to molten salt.

3. The method of claim 1, wherein the outer surface of the tubular member is attached to the inner surface of the tubular fixture by an adhesive.

4. The method of claim 1, wherein the heating of the tubular member and the tubular fixture is performed by subjecting the components to a heated acid solution.

5. The method of claim 4, wherein the tubular member is made from stainless steel.

6. The method of claim 1, further including:
water quenching the tubular member and tubular fixture after heating;
subjecting the tubular member and tubular fixture to heated water; and
subjecting the tubular member and tubular fixture to ultrasonic vibration.

7. The method of claim 6, wherein the tubular member is made from aluminum.

8. A method for making a device, the method comprising:
selecting a tubular member made from a particular metallic material which will be formed into the device;

selecting a shielding gas which will cooperate with a laser source to selectively cut the tubular member;

directing the shielding gas to move portions of the tubular member which is melted by the laser source;

subjecting the tubular member to the shielding gas and cutting a pattern into the tubular member using a laser source, wherein the shielding gas is capable of doping the portion of the tubular member which becomes melted during laser cutting to create brittle slag when the melted portion of the tubular member resolidifies.

9. The method of claim 8, further including:

selecting a secondary gas which dopes the melted portion of the tubular member to create brittle slag when the melted portion of the tubular member resolidifies; and simultaneously subjecting the melted portion of the tubular member to the secondary gas.

10. The method of claim 8, wherein a powder is mixed in with the shielding gas.

11. The method of claim 10, wherein the powder is alumina.

12. The method of claim 10, wherein the powder is carbon.

13. A method for making a laser cut device, the method comprising:

providing a tubular member made from a nickel-titanium alloy which will be formed into the laser cut device, the tubular member having a particular inner diameter;

providing a sacrificial sleeve having an outer diameter which is larger than the diameter of the tubular member;

cooling the tubular member to transformed the tubular member from its Austenitic phase to its Martensitic phase;

placing the tubular member co-axially over the sacrificial sleeve while the tubular member is in the Martensitic phase;

heating the tubular member back to its Austenitic phase; and selectively removing portions of the tubular member and sacrificial sleeve.

14. The method of claim 13, wherein the sacrificial sleeve is initially mounted onto a mandrel.

15. The method of claim 14, wherein the mandrel is removed from the sacrificial sleeve before the tubular member is heated back to its Austenitic phase.

16. A method for making a device, the method comprising:

providing a tubular member with an inner lumen which will be formed into the device;

pressurizing the inner lumen of the tubular member with a gas;

cutting a pattern into the tubular member using a laser, wherein the laser source uses a shielding gas to assist in the laser cutting process and the pressure of the gas pressurizing the tubular member is higher than the pressure placed on the tubular member by the laser source and shielding gas.

17. A method for making a device, the method comprising:

providing a tubular member with an inner lumen which will be formed into the device;

pressurizing the inner lumen of the tubular member with a gas;

cutting a pattern into the tubular member using a laser, wherein the pressurizing gas and a shielding gas are the same gas.

18. A method for making a device, the method comprising:

providing a tubular member with an inner lumen which will be formed into the device;

pressurizing the inner lumen of the tubular member with a gas;

cutting a pattern into the tubular member using a laser, wherein one end of the tubular member has a plug inserted into its inner lumen to help maintain the inner lumen pressurized and the other end of the tubular member is in communication with a pressure source.

19. The method of claim 18, wherein the tubular member is moved in order to cut the pattern into the tubular member and the plug is movable within the inner lumen of the tubular member.

20. The method of claim 18, wherein the plug is adapted to minimize the amount of pressured gas which is exiting the inner lumen of the tubular member as the laser source cuts the pattern into the portion of the tubular member.

* * * * *